(12) United States Patent  
Ando et al.

(10) Patent No.: US 12,600,037 B2  
(45) Date of Patent: Apr. 14, 2026

(54) REMOTE CONTROL ROBOT, REMOTE CONTROL ROBOT CONTROL SYSTEM, AND REMOTE CONTROL ROBOT CONTROL METHOD

(71) Applicant: NTT, Inc., Tokyo (JP)

(72) Inventors: Dai Ando, Musashino (JP); Narimune Matsumura, Musashino (JP)

(73) Assignee: NTT, Inc., Tokyo (JP)

( * ) Notice: Subject to any disclaimer, the term of this patent is extended or adjusted under 35 U.S.C. 154(b) by 190 days.

(21) Appl. No.: 18/571,363

(22) PCT Filed: Jun. 18, 2021

(86) PCT No.: PCT/JP2021/023250

§ 371 (c)(1),  
(2) Date: Dec. 18, 2023

(87) PCT Pub. No.: WO2022/264421

PCT Pub. Date: Dec. 22, 2022

(65) Prior Publication Data

US 2024/0351204 A1    Oct. 24, 2024

(51) Int. Cl.  
*B25J 9/16* (2006.01)  
*A61G 12/00* (2006.01)  
(Continued)

(52) U.S. Cl.  
CPC ............ *B25J 9/1661* (2013.01); *A61G 12/00* (2013.01); *A61B 34/32* (2016.02); *A61B 34/35* (2016.02);  
(Continued)

(58) Field of Classification Search  
CPC ........ B25J 9/1661; B25J 13/06; B25J 9/1664; B25J 5/00; B25J 13/00; B25J 13/02;  
(Continued)

(56) References Cited

U.S. PATENT DOCUMENTS

2004/0019406 A1* 1/2004 Wang .................... B25J 9/0003  
700/231  
2016/0340867 A1* 11/2016 Matsuzaki ........... A01B 69/008  
(Continued)

FOREIGN PATENT DOCUMENTS

CN        112207838        1/2021  
JP        2010246954        11/2010  
(Continued)

OTHER PUBLICATIONS

Kreczmer, B., et al., "Video conferencing applications for robotic system designed for remote medical examination", Jun. 2015, IEEE, 2015 8th International Conference on Human System Interaction (HSI), pp. 148-154 (Year: 2015).*  
Intuitive.com [online], "da Vinci X Surgical System: Generation 4" available on or before 2018, retrieved on 2018, retrieved from URL<https://www.intuitive.com/ja-jp/-/media/Project/Intuitive-surgical/files/pdf/davinci-x-japan.pdf?la=ja-JP&hash=3BCA359BBD75CBCB9E5A028153F5D114>, 9 pages (with machine translation).

(Continued)

*Primary Examiner* — Abby Lin  
*Assistant Examiner* — Karston G. Evans  
(74) *Attorney, Agent, or Firm* — Fish & Richardson P.C.

(57) ABSTRACT

A remote-controlled robot autonomously travels to a plurality of task execution places according to a patrol schedule and executes a plurality of tasks at each task execution place, and includes a setting acquisition unit, and a first switching unit. The setting acquisition unit acquires setting of whether to perform autonomous operation or to perform manual operation by an operation of an operator from a remote control terminal for each of a plurality of tasks to be executed at each task execution place. The first switching unit switches between task execution by autonomous operation and task execution by manual operation based on the acquired setting.

7 Claims, 33 Drawing Sheets

(51) Int. Cl.

| | |
|---|---|
| *A61B 34/32* | (2016.01) |
| *A61B 34/35* | (2016.01) |
| *G05D 1/80* | (2024.01) |
| *G05D 1/81* | (2024.01) |

(52) U.S. Cl.
CPC ............... *B25J 9/1664* (2013.01); *G05D 1/80* (2024.01); *G05D 1/81* (2024.01)

(58) Field of Classification Search
CPC ........ A61G 12/00; A61B 34/32; A61B 34/35; G05D 1/80; G05D 1/81; G05D 1/02
See application file for complete search history.

(56) References Cited

U.S. PATENT DOCUMENTS

| | | | | |
|---|---|---|---|---|
| 2019/0065970 A1* | 2/2019 | Bonutti | .............. | A61N 1/36514 |
| 2020/0231182 A1* | 7/2020 | Oba | ..................... | G05D 1/0061 |
| 2021/0053229 A1* | 2/2021 | Yuan | ........................ | B25J 13/00 |
| 2021/0163034 A1* | 6/2021 | Gordon | ............. | B60W 50/0098 |
| 2022/0152837 A1* | 5/2022 | Das | ......................... | B25J 13/065 |
| 2024/0253242 A1* | 8/2024 | Sodeyama | ............. | B25J 11/008 |

FOREIGN PATENT DOCUMENTS

| | | | | |
|---|---|---|---|---|
| JP | 201863615 A | | 4/2018 | |
| JP | 202164064 A | | 4/2021 | |
| KR | 20210065442 A | * | 6/2021 | ........... B25J 19/023 |

OTHER PUBLICATIONS

Shinyuri-hospital.com [online], "What is da Vinci? I Center for Robotic Surgery (da Vinci)" available on or before Jun. 30, 2015, retrieved on May 2021, retrieved from URL<https://www.shinyuri-hospital.com/advanced_medical_technology/davinci.html>, 9 pages (with machine translation).

Softbank.jp [online], "Robot Product Specifications," available on or before Oct. 9, 2015, retrieved on May 2021, retrieved from URL<https://www.softbank.jp/robot/consumer/products/spec/>, 5 pages (with machine translation).

ZMP.co.jp [online], "Unmanned security/disinfection robot 'PATORO'", available on or before May 24, 2020, retrieved on May 2021, retrieved from URL<https://www.zmp.co.jp/products/lrb/patoro>, 33 pages (with machine translation).

* cited by examiner

Fig. 4

| ROBOT NUMBER | DATE | START TIME | PATROL ORDER 1 | PATROL ORDER 2 | PATROL ORDER 3 | PATROL ORDER 4 |
|---|---|---|---|---|---|---|
| R01 | 2021/3/1 | 9:00 | 101: A | 102: B | 103: C | COMPLETION |
| R02 | 2021/3/1 | 13:00 | 201: D | 202: E | COMPLETION | |
| ⋮ | ⋮ | ⋮ | ⋮ | ⋮ | ⋮ | ⋮ |

Fig. 5

| TASK NUMBER | TASK FUNCTION NAME | AUTOMATIC/ MANUAL FLAG |
|---|---|---|
| 001 | ROOM TEMPERATURE MEASUREMENT | AUTOMATIC |
| 002 | BODY TEMPERATURE MEASUREMENT (NON-CONTACT) | AUTOMATIC |
| 003 | BLOOD PRESSURE MEASUREMENT | MANUAL |
| 004 | INTERVIEW | MANUAL |
| ⋮ | ⋮ | ⋮ |

Fig. 6

| DATE | TIME | ROOM NUMBER | ROOM TEMPERATURE | BODY TEMPERATURE | BLOOD PRESSURE | INTERVIEW | REMARKS |
|---|---|---|---|---|---|---|---|
| 2021/3/1 | 9:05 | 101 | 18.0 | 36.5 | 90 / 120 | YES | |
| 2021/3/1 | 15:03 | 101 | 20.0 | 36.5 | 87 / 119 | YES | |
| ⋮ | ⋮ | ⋮ | ⋮ | ⋮ | ⋮ | ⋮ | ⋮ |

ROBOT CONTROL TERMINAL FUNCTION UNIT ~ 30

31 — PATROL PREDICTION/TASK SETTING UNIT

KB/MOUSE ~ 341

32 — VIDEOPHONE FUNCTION UNIT    322

MONITOR ~ 342

321 — CALL FUNCTION UNIT    VIDEO/AUDIO COMMUNICATION FUNCTION UNIT

CAMERA ~ 343

MICROPHONE ~ 344

33 — ROBOT OPERATION FUNCTION UNIT    332

331 — ARM PORTION OPERATION UNIT    MOVEMENT OPERATION UNIT

SPEAKER ~ 345

333 — CAMERA OPERATION UNIT

OPERATION DEVICE ~ 346

| TASK NUMBER | TASK FUNCTION NAME | AUTOMATIC/ MANUAL FLAG | OPTION FLAG 1 | OPTION FLAG 2 |
|---|---|---|---|---|
| 001 | ROOM TEMPERATURE MEASUREMENT | AUTOMATIC | | |
| 002 | BODY TEMPERATURE MEASUREMENT (NON-CONTACT) | AUTOMATIC | * | |
| 003 | BLOOD PRESSURE MEASUREMENT | MANUAL | | * |
| 004 | INTERVIEW | MANUAL | | * |
| ⋮ | ⋮ | ⋮ | ⋮ | ⋮ |

Fig. 16

| DATE | TIME | ROOM NUMBER | ROOM TEMPERATURE | BODY TEMPERATURE | BLOOD PRESSURE | INTERVIEW | REMARKS |
|---|---|---|---|---|---|---|---|
| 2021/3/1 | 9:05 | 101 | 18.0 | 36.5 | 90 / 120 | YES | |
| 2021/3/1 | 15:03 | 101 | 20.0 | 36.5 | — | — | sleep |
| ⋮ | ⋮ | ⋮ | ⋮ | ⋮ | ⋮ | ⋮ | ⋮ |

| ROBOT NUMBER | DATE | START TIME | PATROL ORDER 1 | PATROL ORDER 2 | PATROL ORDER 3 | PATROL ORDER 4 |
|---|---|---|---|---|---|---|
| R01 | 2021/3/1 | 9:00 | 101: A | 102: B | 103: C | COMPLETION |
| R02 | 2021/3/1 | 13:00 | 201: D | 202: E | COMPLETION | |
| ⋮ | ⋮ | ⋮ | ⋮ | ⋮ | ⋮ | ⋮ |

| ROBOT NUMBER | DATE | START TIME | PATROL ORDER 1 | PATROL ORDER 2 | PATROL ORDER 3 | PATROL ORDER 4 | PATROL ORDER 5 |
|---|---|---|---|---|---|---|---|
| R01 | 2021/3/1 | 9:00 | 101: A | 102: B | 103: C | 101: A | COMPLETION |
| R02 | 2021/3/1 | 13:00 | 201: D | 202: E | COMPLETION | | |
| ⋮ | ⋮ | ⋮ | ⋮ | ⋮ | ⋮ | ⋮ | ⋮ |

Fig. 24

| NURSE NUMBER | NURSE SKILL |
|---|---|
| N001 | HIGH SKILL |
| N002 | LOW SKILL |
| ⋮ | ⋮ |

REMOTE CONTROL ROBOT, REMOTE CONTROL ROBOT CONTROL SYSTEM, AND REMOTE CONTROL ROBOT CONTROL METHOD

CROSS-REFERENCE TO RELATED APPLICATIONS

This application is a National Stage application under 35 U.S.C. § 371 of International Application No. PCT/JP2021/023250, having an International Filing Date of Jun. 18, 2021, the disclosure of which is considered part of the disclosure of this application, and is incorporated by reference in its entirety into this application.

TECHNICAL FIELD

Embodiments of the present invention relate to a remote-controlled robot, a remote-controlled robot control system, and a remote-controlled robot control method.

BACKGROUND ART

In recent years, robot technology and AI technology have developed, and development of an autonomous control type remote-controlled robot capable of autonomously executing a task has been progressed, and in particular tasks, the robot has been put into practical use, and the efficiency of the task has been improved.

For example, NPL 1 describes an example of an automatic reception robot. The automatic reception robot has a camera, a monitor, a microphone, a speaker, and an automatic response function on the robot side, and performs automatic response to a visitor based on an automatic response program stored in the robot control server (for example, reception work or the like).

NPL 2 describes an example of an automatic patrol robot. The automatic patrol robot has a drive unit and an automatic patrol function on the robot side, and performs automatic patrol task (patrol/monitoring task or the like) based on patrol prediction information stored in a robot control server.

On the other hand, in the technical field of tasks such as those in medical care, the robot has not yet reached a level at which the robot can autonomously (completely) automatically perform the tasks. For this reason, a highly functional manually controlled remote-controlled robot has been developed for an operator having a professional skill such as a doctor or the like to manually operate a remote robot and perform advanced and complicated tasks such as remote surgery.

For example, NPL 3 and NPL 4 describe an example of a highly functional manually controlled remote-controlled robot. Such a manual control type remote-controlled robot has a camera and a high performance arm (manipulator) on the robot side, and an operator uses an operation device connected to a robot operation terminal from a remote place, and manually controls the operation of the remote robot (for example, remote surgery or the like).

CITATION LIST

Non Patent Literature

[NPL 1] "Product Specifications|Robots|Softbank" [Online], [retrieved on May 17, 2021], the Internet <URL: www.softbank.jp/robot/consumer/products/spec/>

[NPL 2] "Unmanned security and disinfection robot "PATORO"" [Online], [retrieved on May 17, 2021], the Internet <URL: www.zmp.co.jp/products/lrb/patoro>

[NPL 3] "da Vinchi About da Vinchi|Robotic Surgery (Da Vinchi) Center" [Online], [retrieved on May 17, 2021], the Internet <URL: www.shinyuri-hospital.com/advanced_medical_technology/davinci.html>

[NPL 4] "Information on the da Vinci X Surgical System" [Online], [retrieved on May 17, 2021], the Internet <URL: www.intuitive.com/ja-jp/-/media/Project/Intuitive-surgical/files/pdf/davinci-x-japan.pdf?la-ja-JP&hash=3BCA359BBD75CBCB9E5A028153F5D114>

SUMMARY OF INVENTION

Technical Problem

In the case of an autonomous control type remote-controlled robot as disclosed in above-mentioned NPL 1 and NPL 2, remote control can be performed with respect to a predetermined function and efficiency can be expected, but it is currently available only for routine tasks.

On the other hand, in the case of the manually controlled remote-controlled robot disclosed in above-mentioned NPL 3 and NPL 4, fine control (operation) can be performed from a remote place and the restriction of distance can be reduced, but the robot cannot be operated remotely unless an operator (doctor or the like) always operates directly. Therefore, there is an aspect that work efficiency itself cannot be improved. Further, since the device was developed for advanced and complicated task such as medical care, the device scale becomes large and the costs becomes high, mass production is difficult, and introduction into tasks is difficult.

As described above, the remote-controlled robot is bipolar for a task suitable for autonomous control such as the robot disclosed in above-mentioned NPL 1 and NPL 2, and for a task suitable for manual control such as the robot disclosed in above-mentioned NPL 3 and NPL 4. Therefore, it is difficult to introduce these remote-controlled robots in a case where the tasks for autonomous control and the tasks for manual control coexist.

That is, in a case where the remote-controlled robot is intended to be utilized in a task in which a task directed to autonomous control and a task directed to manual control coexist, both the autonomous control task function and the manual control task function must be implemented, and they must be appropriately controlled. For example, in nursing tasks, a routine task such as room temperature management in a sickroom and management of vital data (body temperature or the like) of a patient, and work requiring careful consideration of the human partner who is a patient. Further, since the condition of the patient is different for each patient, it is necessary to control (switch between or the like) using an autonomous control function and a manual control function for each patient.

However, since such a remote-controlled robot has not been realized at present, in a facility in which tasks directed to autonomous control and tasks directed to manual control are mixed, such as nursing tasks, the efficiency of the task by utilizing a remote-controlled robot has not been realized.

The present invention aims to provide a technique that enables the introduction of a remote-controlled robot even to a facility in which tasks directed to autonomous control and tasks directed to manual control coexist.

Solution to Problem

In order to solve the above problem, a remote-controlled robot according to an embodiment of the present invention autonomously travels to a plurality of task execution places according to a patrol schedule and executes a plurality of tasks at each task execution place, the robot including a setting acquisition unit that acquires settings of whether to perform autonomous operation or to perform manual operation by the operation of an operator from a remote control terminal for each of a plurality of tasks to be performed at each task execution place and a first switching unit that switches between task execution by the autonomous operation and task execution by the manual operation based on the acquired setting.

Advantageous Effects of Invention

According to an aspect of the present invention, the remote-controlled robot is made to automatically perform a task autonomously performed by the remote-controlled robot, and only a task to be manually performed by an operator can be manually performed from a remote place, so that a technique capable of introducing the remote-controlled robot even to a facility in which a task directed to autonomous control and a task directed to manual control coexist can be provided.

BRIEF DESCRIPTION OF DRAWINGS

FIG. 4 is a diagram illustrating an example of a content of a patrol schedule table in FIG. 3.

FIG. 5 is a diagram illustrating an example of a content of a task function setting table in FIG. 3.

FIG. 6 is a diagram illustrating an example of a content of a measurement recording table in FIG. 3.

FIG. 15 is a diagram illustrating an example of a content of a task function setting table in the second embodiment.

FIG. 16 is a diagram illustrating an example of a content of a measurement recording table in the second embodiment.

FIG. 24 is a diagram illustrating an example of a content of a nurse skill information table in FIG. 23.

DESCRIPTION OF EMBODIMENTS

Hereinafter, embodiments of the present invention will be described with reference to the drawings. In the following embodiments, a case where a remote-controlled robot 1 executes nursing tasks in a hospital will be described as an example, but it is needless to say that the present invention can be applied to tasks in other facility.

First Embodiment (Configuration)

Figure 1:
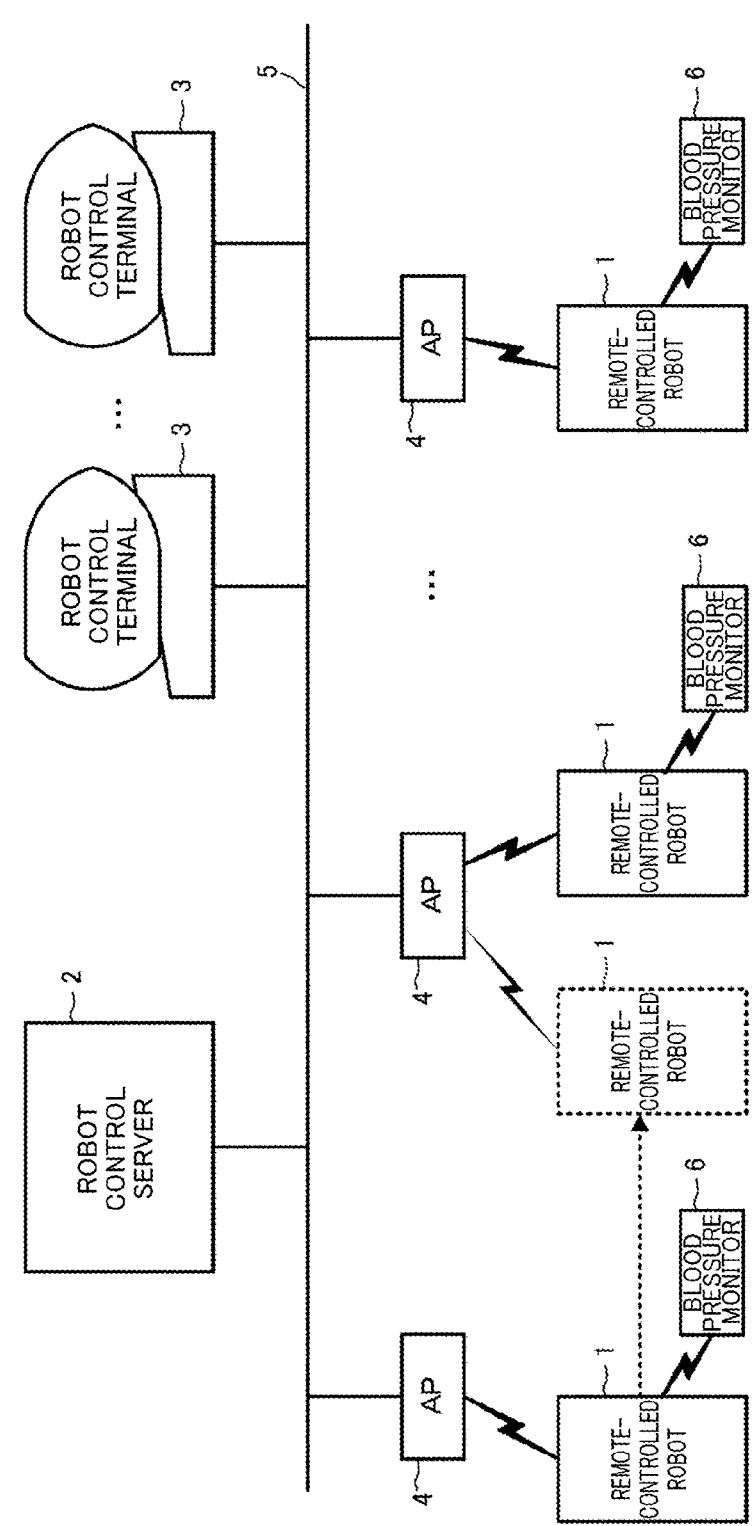
FIG. 1 is a schematic diagram illustrating a remote-controlled robot control system according to a first embodiment of the present invention.

FIG. 1 is a schematic diagram illustrating a remote-controlled robot control system according to a first embodiment of the present invention.

The remote-controlled robot control system includes one or more remote-controlled robots 1, a robot control server 2, one or more robot control terminals 3, and one or more access points (indicated by AP in FIG. 1) 4. The remote-controlled robot 1, the robot control server 2, the robot control terminal 3 and the access point 4 are connected to a network 5 such as a local area network (LAN). In addition, the remote-controlled robot control system may also include one or more blood pressure monitors 6.

The remote-controlled robot 1 is a remote-controlled robot according to a first embodiment of the present invention. The robot control server 2 stores control information for controlling each operation of the remote-controlled robot 1. The robot control terminal 3 is a terminal to which a nurse as an operator inputs the control information in the robot control server 2 and operates the remote-controlled robot 1 to manually control the remote-controlled robot 1. The access point 4 relays communication between the robot control server 2 and the robot control terminal 3 connected to the network 5 and the remote-controlled robot 1 by communicating with the remote-controlled robot 1. The access point 4 is arranged to cover the whole moving range of the remote-controlled robot 1. In FIG. 1, the movement of the remote-controlled robot 1 is indicated by a broken line. The blood pressure monitor 6 has a communication function with the remote-controlled robot 1.

Figure 2:
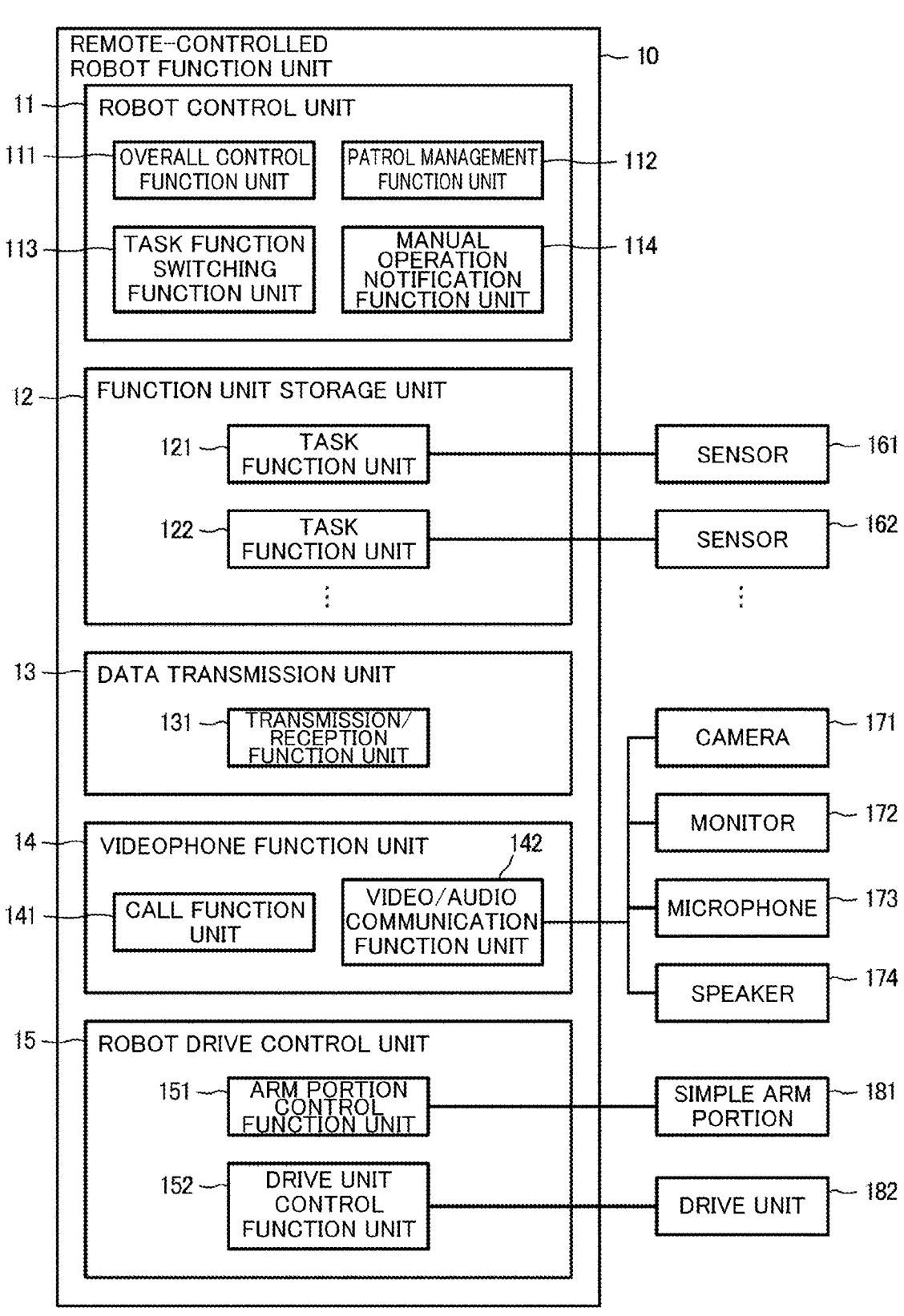
FIG. 2 is a block diagram illustrating an example of a functional configuration of a remote-controlled robot according to the first embodiment.

FIG. 2 is a block diagram illustrating a functional configuration of the remote-controlled robot 1 according to the first embodiment.

The remote-controlled robot 1 includes a remote-controlled robot function unit 10 including a robot control unit 11, a function unit storage unit 12, a data transmission unit 13, a videophone function unit 14, and a robot drive control unit 15. Further, the remote-controlled robot 1 includes various sensors 161, 162, . . . as detection units, a camera 171, as an interface unit with a user who is a patient, a monitor 172, a microphone 173, and a speaker 174, and a drive unit 182 and a simple arm portion 181 which are mechanical units. The drive unit 182 is, for example, wheels or the like. The simple arm portion 181 is a manipulator or the like.

The robot control unit 11 includes an overall control function unit 111, a patrol management function unit 112, a task function switching function unit 113, and a manual operation notification function unit 114. The overall control function unit 111 controls the overall operation of the remote-controlled robot 1. The patrol management function unit 112 controls an intra-facility patrol operation of the remote-controlled robot 1. The task function switching function unit 113 controls switching of tasks executed by the remote-controlled robot 1. The manual operation notification function unit 114 notifies the robot control terminal 3 that the remote-controlled robot 1 has come to a timing for executing switching from autonomous control to manual control.

The function unit storage unit 12 includes task function units (a task function unit 121, a task function units 122, . . . ) corresponding to various kinds of task. The task function units 121, 122, . . . are connected to related external sensors 161, 162, . . . . For example, the task function unit 121 can be a room temperature measuring function, the sensor 161 can be a room temperature meter, the task function unit 122 can be a body temperature measuring function in a non-contact manner, and the sensor 162 can be a non-contact thermometer.

The data transmission unit 13 includes a transmission/reception function unit 131 for transmitting the acquired data to the robot control server 2.

The videophone function unit 14 includes a call function unit 141 and a video/audio communication function unit 142. The call function unit 141 calls the robot control terminal 3. The video/audio communication function unit 142 is connected to the camera 171, the monitor 172, the microphone 173, and the speaker 174, and performs video/audio communication with the robot control terminal 3.

The robot drive control unit 15 includes an arm portion control function unit 151 and a drive unit control function unit 152. The arm portion control function unit 151 is connected to the simple arm portion 181, and controls movement of the simple arm portion 181 according to operation information from the robot control terminal 3. The drive unit control function unit 152 is connected to the drive unit 182 such as wheels, and makes the remote-controlled robot 1 autonomously travel according to a patrol route stored in the robot control server 2. The drive unit control function unit 152 can also control the drive unit 182 according to operation information from the robot control terminal 3.

Although not illustrated in particular, the remote-controlled robot 1 may include a camera direction movement unit for changing the direction of the camera 171 as a mechanical unit. In this case, the robot drive control unit 15 can include a camera direction control function unit that controls the camera direction movement unit according to operation information from the robot control terminal 3. Thus, for example, when moving the simple arm portion 181 from the robot control terminal 3, the direction of the camera 171 can be changed to capture the simple arm portion 181 in a camera visual field.

Figure 3:
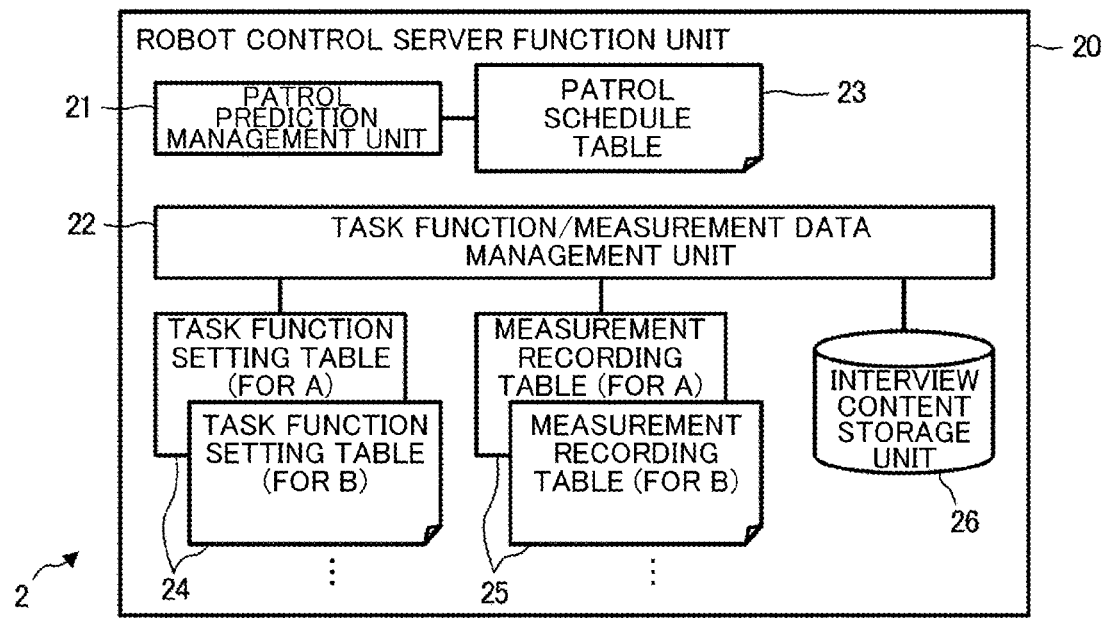
FIG. 3 is a block diagram illustrating an example of a functional configuration of a robot control server in FIG. 1.

FIG. 3 is a block diagram illustrating an example of the functional configuration of the robot control server 2. The robot control server 2 includes a patrol prediction management unit 21 and a task function/measurement data management unit 22.

The patrol prediction management unit 21 manages a schedule (patrol prediction) for each remote-controlled robot 1 to patrol a sickroom using a patrol schedule table 23. That is, the patrol prediction management unit 21 records the patrol schedule of each remote-controlled robot 1 input from the robot control terminal 3 in the patrol schedule table 23, and transmits the corresponding patrol schedule to each remote-controlled robot 1.

The task function/measurement data management unit 22 manages at least one task function setting table 24, at least one measurement recording table 25, and an interview content storage unit 26. The task function setting table 24 and the measurement recording table 25 are provided for each hospitalized patient, for example. In the task function setting table 24, the automatic/manual setting contents of various tasks input from the robot control terminal 3 are recorded. In the measurement recording table 25, the measurement data measured and transmitted by the remote-controlled robot 1 is recorded. The interview content storage unit 26 stores interview contents input from the robot control terminal 3.

FIG. 4 is a diagram illustrating an example of a content of the patrol schedule table 23.

The patrol schedule table 23 is configured to, for example, associate with a robot number of the managed remote-controlled robot 1, a date and a start time of starting patrol work, and in the patrol schedule table, the number of each sickroom to be patrolled and the patient's name are listed in a patrol order. In addition, the end of the patrol is described as "Completion". Here, although the robot numbers are [R01], [R02], . . . , any type of the remote-controlled robot 1 such as a manufacturing number may be used as long as the robot 1 can be uniquely identified. In addition, in the drawings, although A, B, . . . represent patient names and one patient exists in one room, a plurality of names may be present. In a case where there are a plurality of names, a bed number or the like may be listed in addition to the sickroom number.

FIG. 5 is a diagram illustrating an example of a content of the task function setting table 24.

The task function setting table 24 is provided for each patient, and for each task function to be executed, for example, items of a task number, the task function name and an automatic/manual flag are described. The automatic/manual flag is described as [Automatic] in a case where the corresponding task function is automatically executed for the patient, and [Manual] in a case where the task function is manually executed. Of course, other methods may be used, for example, to simply express automatic/manual operation by [1]/[0].

FIG. 6 is a diagram illustrating an example of a content of the measurement recording table 25.

The measurement recording table 25 is provided for each patient, and describes, for example, items such as dates, time, a room number, a room temperature, a body temperature, a blood pressure, an interview, or remarks. In the items of the interview, whether the interview has been made or not with the nurse of the robot control terminal 3 is described by the videophone function unit 14. In the item of remarks, a sentence or the like input by the nurse from the robot control terminal 3 can be described.

Figure 7:
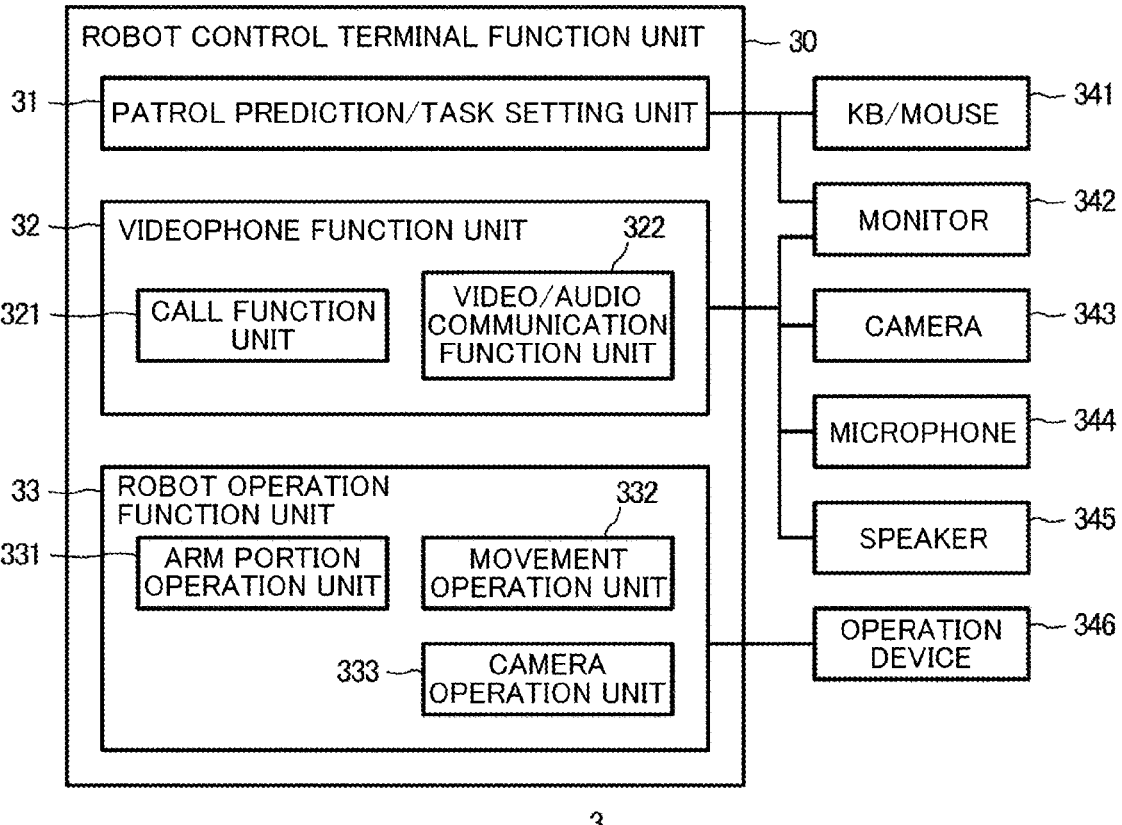
FIG. 7 is a block diagram illustrating an example of a functional configuration of a robot control terminal in FIG. 1.

FIG. 7 is a block diagram illustrating an example of the functional configuration of the robot control terminal 3.

The robot control terminal 3 includes a robot control terminal function unit 30 including a patrol prediction/task setting unit 31, a videophone function unit 32, and a robot operation function unit 33. Further, the robot control terminal 3 includes a keyboard (illustrated as KB in FIG. 7)/mouse 341, a monitor 342, a camera 343, a microphone 344, a speaker 345, and an operation device 346 which are interface units of a user who is a nurse.

The patrol prediction/task setting unit 31 is connected to the keyboard/mouse 341 and the monitor 342, and reads out the setting of the patrol schedule table 23 and the task function setting table 24 in the robot control server 2 and the contents of the measurement recording table 25 and displays them on the monitor 342 to make a nurse refer to the respective contents. In addition, the patrol prediction/task setting unit 31 receives automatic/manual input of patrol prediction and various tasks by the operation of the keyboard/mouse 341 of a nurse, transmits the input contents to the robot control server 2, thereby reflecting the input contents on the patrol schedule table 23, the task function setting table 24 and the measurement recording table 25.

The videophone function unit 32 is connected to the monitor 342, the camera 343, the microphone 344, and the speaker 345, and includes a call reception function unit 321 and a video/audio communication function unit 322. The call reception function unit 321 receives the call from the remote-controlled robot 1, and notifies the nurse of the reception of the call by the monitor 342 and the speaker 345. The video/audio communication function unit 322 performs video/audio communication with the patient via the remote-controlled robot 1.

The robot operation function unit 33 is connected to the operation device 346, and includes an arm portion operation function unit 331 and a movement operation function unit 332 for remotely controlling the simple arm portion 181 and the drive unit 182 (wheels or the like) of the remote-controlled robot 1. In addition, the robot operation function unit 33 can include a camera operation function unit 333 for remotely controlling the camera 171 in a case where the remote-controlled robot 1 includes a camera direction movement unit for changing the direction of the camera 171 as a mechanical unit.

Figure 8:
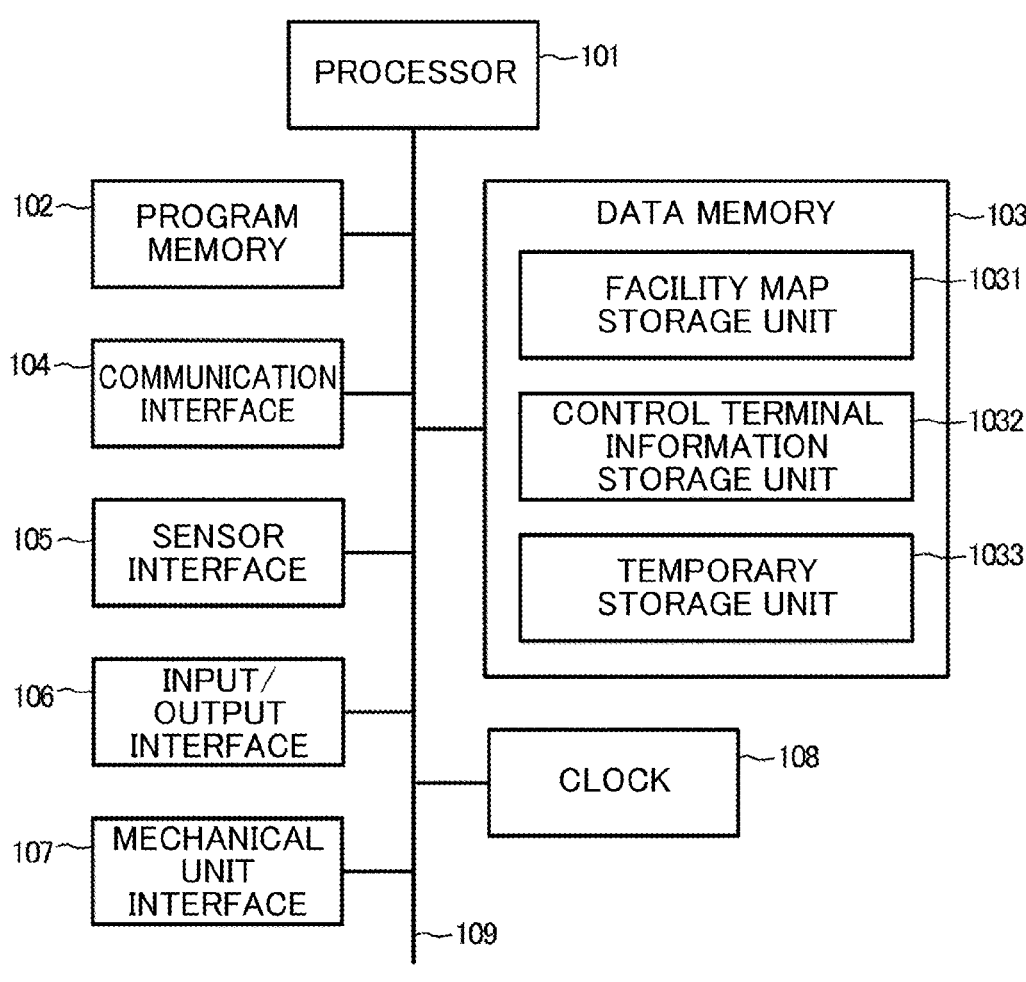
FIG. 8 is a diagram illustrating an example of a hardware configuration of a computer that implements the functional configuration of the remote-controlled robot in FIG. 2.

FIG. 8 is a diagram illustrating an example of a hardware configuration of a computer which implements the functional configuration of the remote-controlled robot 1.

The remote-controlled robot 1 includes a hardware processor 101 such as a central processing unit (CPU). In the remote-controlled robot 1, a program memory 102, a data memory 103, a communication interface 104, a sensor interface 105, an input/output interface 106, a mechanical unit interface 107, and a clock 108 are connected to the processor 101 via a bus 109. The CPU can simultaneously execute a plurality of information processing using multi-core and multi-thread. In addition, the processor 101 may include a plurality of CPUs.

The program memory 102 is, for example, a combination of non-volatile memory such as an HDD (hard disk drive) or a solid state drive (SSD) that can be written and read at any time and non-volatile memory such as ROM as a non-transitory tangible computer-readable storage medium. The program memory 102 stores control programs necessary for the processor 101 to execute various control processes according to the present embodiment. For example, the robot control unit 11, the function unit storage unit 12, the data transmission unit 13, the videophone function unit 14, and the robot drive control unit 15 are realized by causing the processor 101 to read out and execute the processing program stored in the program memory 102. A part or all of these processing function units may be realized in various other forms including integrated circuits such as application specific integrated circuits (ASIC) or FPGA (field-programmable gate array).

As the data memory 103, a tangible computer-readable storage medium is used, for example, in which the above-described non-volatile memory and a volatile memory such as a RAM (random access memory) are combined. The data memory 103 is used to store various types of data acquired and created during the execution of various types of processing. For example, in the data memory 103, a storage area such as a facility map storage unit 1031, a control terminal information storage unit 1032, or a temporary storage unit 1033 is secured.

The temporary storage unit 1033 is a storage area for temporarily storing various types of data generated in a process in which the processor 101 executes various control processing.

The facility map storage unit 1031 stores map information such as room arrangement and bed position in a hospital. Further, the facility map storage unit 1031 can store information necessary for autonomous traveling and autonomous task execution, such as the names of hospitalized patients in the beds of the rooms. These pieces of information can be acquired and stored from, for example, a hospital management server (not illustrated) connected to the network 5. Further, the facility map storage unit 1031 may be not provided, but may be obtained by communicating with a hospital management server or the like as necessary, and temporarily stored in the temporary storage unit 1033.

The control terminal information storage unit 1032 stores information for specifying the robot control terminal 3 for manually controlling the remote-controlled robot 1. Based on the information, manual control can be received from one or more robot control terminals 3 arranged at various places in the hospital by communicating with the corresponding robot control terminal 3.

The communication interface 104 is a wireless communication module for transmitting and receiving information between the access point 4 and the blood pressure monitor 6.

The sensor interface 105 is an input module for connecting the sensors 161, 162, . . . to receive sensor data.

The input/output interface 106 is an input/output module for connecting the camera 171, the monitor 172, the microphone 173, and the speaker 174.

The mechanical unit interface 107 is an output module for connecting the simple arm portion 181 and the drive unit 182.

The clock 108 counts the current date and time.

Figure 9:
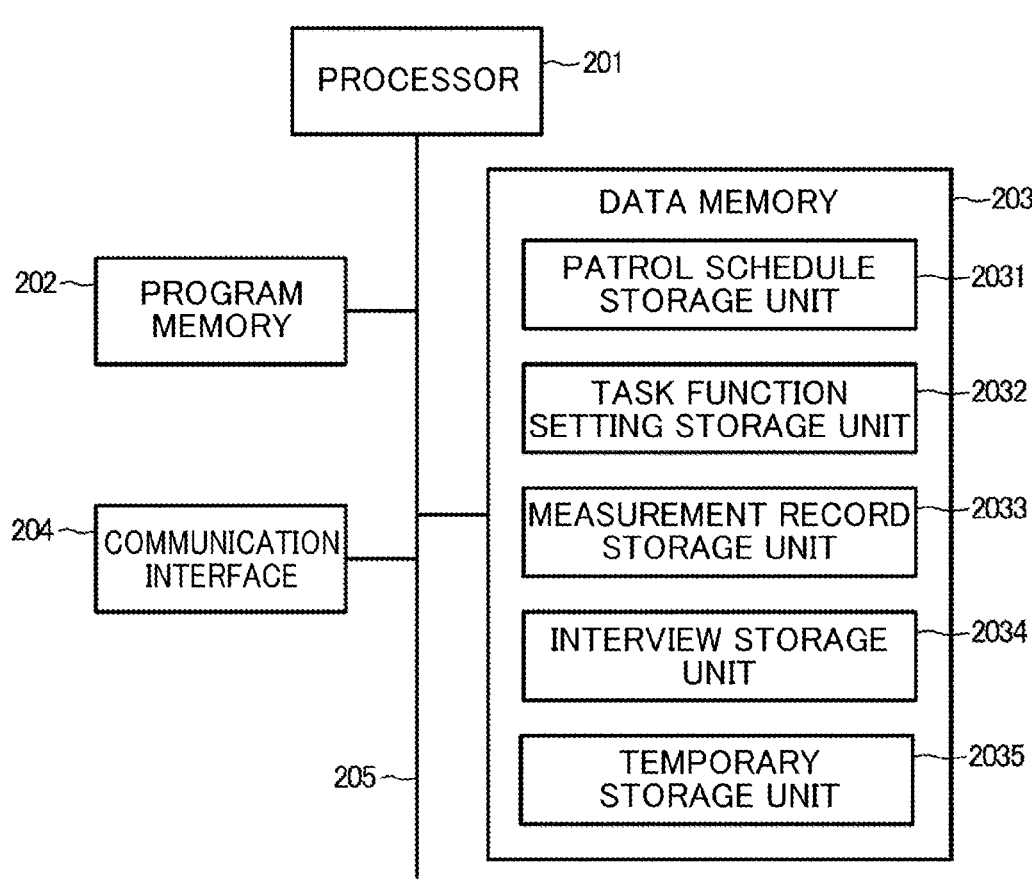
FIG. 9 is a diagram illustrating an example of a hardware configuration of a computer which implements a functional configuration of a robot control server of FIG. 4.

FIG. 9 is a diagram illustrating an example of a hardware configuration of a computer which implements a functional configuration of the robot control server 2.

The robot control server 2 has a hardware processor 201 such as a CPU. In the robot control server 2, a program memory 202, a data memory 203, and a communication interface 204 are connected to the processor 201 via a bus 205. The CPU can simultaneously execute a plurality of information processing using multi-core and multi-thread. In addition, the processor 201 may include a plurality of CPUs.

The program memory 202 is, for example, a combination of non-volatile memory such as an HDD or an SSD that can be written and read at any time and non-volatile memory such as ROM as a non-transitory tangible computer-readable storage medium. The program memory 202 stores control programs necessary for the processor 201 to execute various control processes according to the present embodiment. For example, the patrol prediction management unit 21 and the task function/measurement data management unit 22 are realized by causing the processor 201 to read out and execute the processing program stored in the program memory 202. A part or all of these processing function units may be realized in various other forms including integrated circuits such as an ASIC or a FPGA.

As the data memory 203, a tangible computer-readable storage medium is used, for example, in which the above-described non-volatile memory and a volatile memory such as a RAM are combined. This data memory 203 is used to store various types of data acquired and generated during the execution of various types of processing. For example, in the data memory 203, a storage area such as a patrol schedule storage unit 2031, a task function setting storage unit 2032, a measurement record storage unit 2033, an interview storage unit 2034, or a temporary storage unit 2035 is secured.

The temporary storage unit 2035 is a storage area for temporarily storing various types of data generated in a process in which the processor 201 executes various control processing.

The patrol schedule storage unit 2031 is a storage area for storing the patrol schedule table 23.

The task function setting storage unit 2032 is a storage area for storing the task function setting table 24 for each patient. In addition, the measurement record storage unit 2033 is a storage area for storing the measurement recording table 25 for each patient.

The interview storage unit 2034 is a storage area that functions as the interview content storage unit 26.

The communication interface 204 is a wired or wireless communication module for connecting with the network 5 and performing communication via the network 5.

Figure 10:
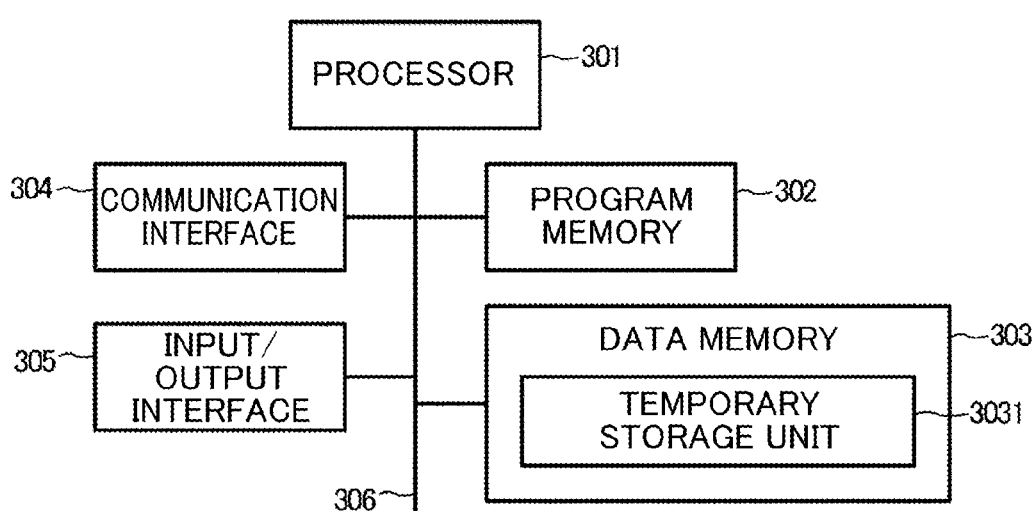
FIG. 10 is a diagram illustrating an example of a hardware configuration of a computer which implements a functional configuration of a robot control terminal of FIG. 7.

FIG. 10 is a diagram illustrating an example of a hardware configuration of a computer which implements a functional configuration of the robot control terminal 3.

The robot control terminal 3 has a hardware processor 301 such as a CPU. In the robot control terminal 3, a program memory 302, a data memory 303, a communication interface 304, and an input/output interface 305 are connected to the processor 301 via a bus 306. The CPU can simultaneously execute a plurality of information processing using multi-core and multi-thread. In addition, the processor 301 may include a plurality of CPUs.

The program memory 302 is, for example, a combination of non-volatile memory such as an HDD or an SSD that can be written and read at any time and non-volatile memory such as ROM as a non-transitory tangible computer-readable storage medium. The program memory 302 stores control programs necessary for the processor 301 to execute various control processes according to the present embodiment. For example, the patrol prediction/task setting unit 31, the videophone function unit 32, and the robot operation function unit 33 are realized by causing the processor 301 to read out and execute the processing program stored in the program memory 302. A part or all of these processing function units may be realized in various other forms including integrated circuits such as an ASIC or a FPGA.

As the data memory 303, a tangible computer-readable storage medium is used, for example, in which the above-described non-volatile memory and a volatile memory such as a RAM are combined. This data memory 303 is used to store various types of data acquired and generated during the execution of various types of processing. For example, in the data memory 303, a temporary storage unit 3031 which is a storage area for temporarily storing various types of data generated in the process of executing various control processing by the processor 301.

The communication interface 304 is a wired or wireless communication module for connecting with the network 5 and performing communication via the network 5.

The input/output interface 305 is an input/output module for connecting the keyboard/mouse 341, the monitor 342, the camera 343, the microphone 344, the speaker 345, and the operation device 346.

(Operations)

An operation of a remote-controlled robot control system according to a first embodiment will be described below.

Figure 11:
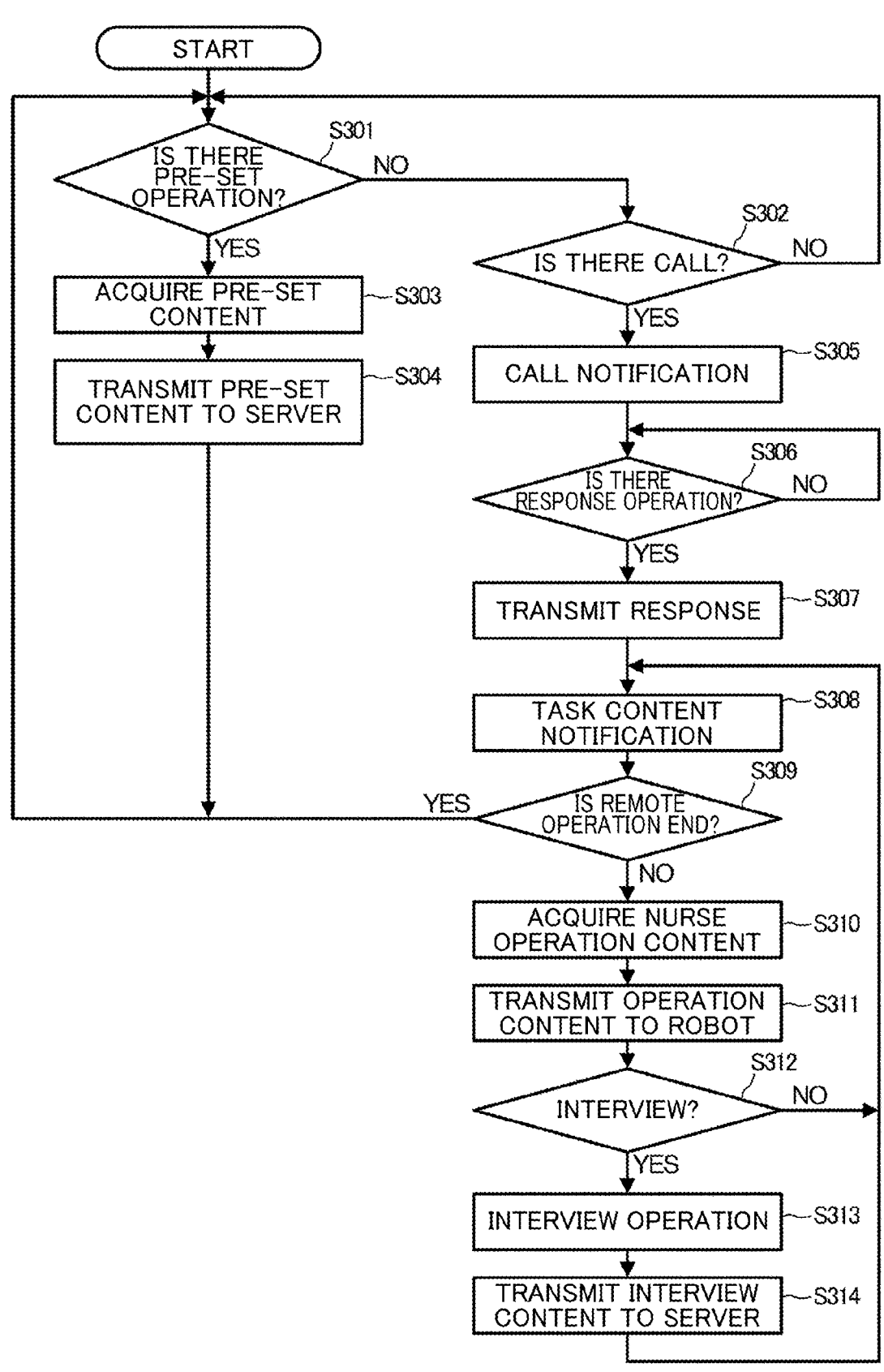
FIG. 11 is a flow chart illustrating an example of an operation of the robot control terminal.

FIG. 11 is a flowchart illustrating an example of an operation of the robot control terminal 3. In a case where the functional configuration of the robot control terminal 3 is realized by a computer as illustrated in FIG. 10, a processing program necessary for executing the control processing illustrated in the flowchart is stored in the program memory 302, and the processor 301 executes the program, thereby operating as the robot control terminal function unit 30 of the robot control terminal 3 as illustrated in FIG. 7.

The processor 301 of the robot control terminal 3 first functions as the patrol prediction/task setting unit 31, and determines whether a pre-set operation from a nurse by the keyboard/mouse 341 connected to the input/output interface 305 is performed (step S301). In a case where it is determined that there is no pre-set operation (NO in step S301), the processor 301 functions as the call reception function unit 321 and determines whether a call is received via the communication interface 304, that is, whether there is a call from the remote-controlled robot 1 (step S302). In a case where it is determined that there is no call (NO in step S302), the processor 301 shifts to the processing of step S301 described above. Thus, the processor 301 waits for a pre-set operation or a call.

(1) Pre-Set Work

In a case where it is determined that the pre-set operation has been performed in the step S301 (YES in step S301), the processor 301 acquires pre-set contents indicating the contents of the pre-set operation performed by the nurse by the keyboard/mouse 341, and stores the content in the temporary storage unit 3031 of the data memory 303 (step S303). Then, the processor 301 transmits the pre-set content to the robot control server 2 by the communication interface 304 (step S304). Next, the processor 301 shifts to the processing in step S301 described above.

Figure 12:
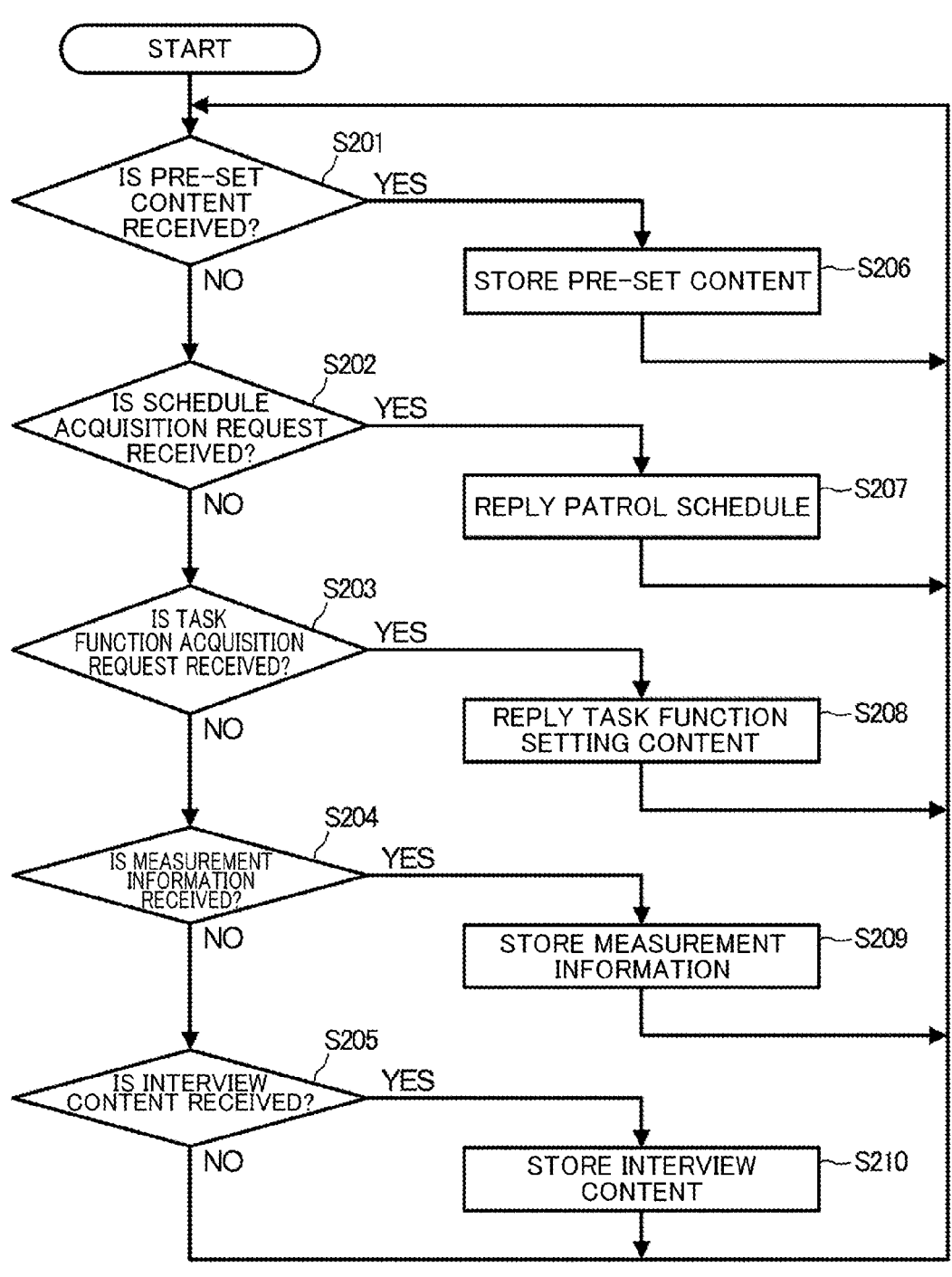
FIG. 12 is a flowchart illustrating an example of an operation of the robot control server.

FIG. 12 is a flowchart illustrating an example of an operation of the robot control server 2. In a case where the functional configuration of the robot control server 2 is realized by a computer as illustrated in FIG. 9, a processing program necessary for executing the control processing illustrated in the flowchart is stored in the program memory 202, and the processor 201 executes the program, thereby operating as the robot control server function unit 20 of the robot control server 2 as illustrated in FIG. 3.

The processor 201 of the robot control server 2 first functions as the patrol prediction management unit 21 and determines whether pre-set contents are received from the robot control terminal 3 by the communication interface 204 (step S201). In a case where it is determined that the pre-set content is not received (NO in step S201), it is determined whether a schedule acquisition request for requesting transmission of a patrol schedule is received from the remote-controlled robot 1 by the communication interface 204 (step S202). In a case where it is determined that the schedule acquisition request is not received (NO in step S202), the processor 201 functions as the task function/measurement data management unit 22, and determines whether the task function acquisition request is received from the remote-controlled robot 1 by the communication interface 204 (step S203). In a case where it is determined that the task function acquisition request is not received (NO in step S203), the processor 201 determines whether the measurement information is received from the remote-controlled robot 1 by the communication interface 204 (step S204). In a case where it is determined that the measurement information is not received (NO in step S204), the processor 201 further determines whether the interview content is received from the robot control terminal 3 by the communication interface 204 (step S205). In a case where it is determined that the interview content is not received (NO in step S205), the processor 201 shifts to the processing of step S201 described above. In this way, the processor 201 waits to receive a pre-set content, a schedule acquisition request, a task function acquisition request, measurement information or an interview content.

In a case where it is determined that the pre-set content is received in the step S201 (YES in step S201), the processor 201 stores the received pre-set content in a patrol schedule storage unit 2031 or the task function setting storage unit 2032 of the data memory 203 (step S206). That is, the pre-set contents are described in the patrol schedule table 23 or the task function setting table 24, or the described contents are updated. Next, the processor 201 shifts to the processing in step S201 described above.

In this way, the pre-set work is performed between the robot control terminal 3 and the robot control server 2. For example, a nurse sets a patrol prediction of each remote-controlled robot 1 in the patrol schedule table 23 in the robot control server 2 using the robot control terminal 3, and/or sets the automatic/manual flag to [Automatic] or [Manual] for each patient in the task function setting table 24 for the nursing task to be performed for each patient in each task. For example, as illustrated in FIG. 5, for the patient A, the task function [Room Temperature Measurement] having the task number [001] and the task function [Body Temperature Measurement] having the task number [002] are set to [Automatic], the task function [Blood Pressure Measurement] having the task number [003] and the task function [Interview] having the task number [004] are set to [Manual].

(2) Start of Patrol Task

Figure 13:
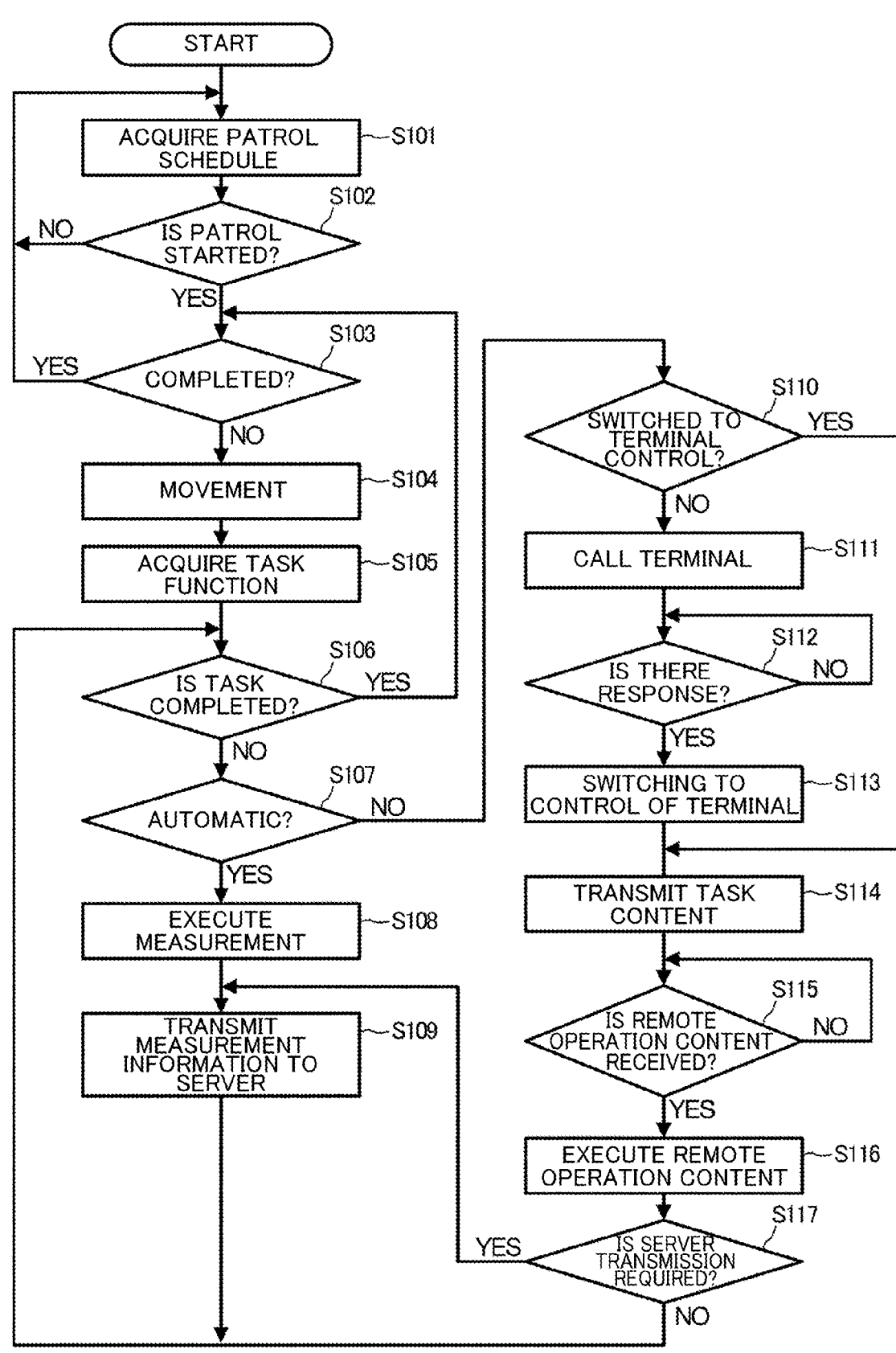
FIG. 13 is a flowchart illustrating an example of an operation of the remote-controlled robot.

FIG. 13 is a flowchart illustrating an example of an operation of the remote-controlled robot 1. In a case where the functional configuration of the remote-controlled robot 1 is realized by a computer as illustrated in FIG. 8, a processing program necessary for executing the control processing illustrated in the flowchart is stored in the program memory 102, and the processor 101 executes the program, thereby operating as the remote-controlled robot function unit 10 of the remote-controlled robot 1 as illustrated in FIG. 2. Specifically, after starting the operation, the processor 101 functions as the robot control unit 11 by executing the control program to perform the following processing.

The processor 101 of the remote-controlled robot 1 functions as the patrol management function unit 112 first, and acquires the remote patrol schedule from the robot control server 2 via the access point 4 by the communication interface 104 (step S101). This is, for example, processing for transmitting a schedule acquisition request including a robot number specifying the remote-controlled robot 1 to the patrol prediction management unit 21 of the robot control server 2, receiving the patrol schedule returned from the patrol prediction management unit 21 by the communication interface 104, and storing the patrol schedule in the temporary storage unit 1033 of the data memory 103.

That is, as illustrated in FIG. 12, in a case where it is determined that the schedule acquisition request is received in the step S202 (YES in step S202), the processor 201 of the robot control server 2 returns the patrol schedule of the remote-controlled robot 1 of the request source by the communication interface 204 (step S207). That is, the processor 201 reads out the patrol schedule set for the robot number included in the schedule acquisition request from the patrol schedule table 23 stored in the patrol schedule storage unit 2031, and transmits the patrol schedule to the remote-controlled robot 1. Next, the processor 201 shifts to the processing in step S201 described above.

Returning to FIG. 13, the processor 101 of the remote-controlled robot 1 determines whether to start the patrol (step S102) after acquiring the patrol schedule in the step S101. This determination can be made depending on whether the current date and time counted by the clock 108 has reached the transmission date and start time of the patrol schedule. In a case where it is determined that the patrol is not started (NO in step S102), the processor 101 shifts to the processing of step S101 described above. Although the processing of the step S102 may be simply repeated until the start time of the acquired patrol schedule is reached, since there is a possibility that the patrol schedule is updated during a period from the acquisition of the patrol schedule to the start time, and processor shifts to the processing of the step S101.

In a case where it is determined that the patrol is started (YES in step S102), the processor 101 confirms the patrol order of the patrol schedule stored in the temporary storage unit 1033, and determines whether [Completion] is set in the patrol order to be executed from now (step S103).

When it is determined that [Completion] is not set (NO in step S103), the processor 101 calculates a movement route to a position of a target patient, functions as a drive unit control function unit 152 and controls the drive unit 182 connected to the mechanical unit interface 107 to move the drive unit to the patient (step S104). The processor 101 can calculate a movement route from the current position based on the patrol order indicated by the patrol schedule and the information stored in the facility map storage unit 1031.

In this way, for example, in the case of the remote-controlled robot 1 having a robot number [R01], after starting the operations, the robot refers to the patrol schedule table 23 in the robot control server 2, confirms the patrol start time and patrol order of the host robot, and when the start time comes, the robot starts patrol task by automatic traveling using the drive unit 182, and heads for patrol of patient A in Room 101, which is patrol order 1.

(3) Execution of Task Function

When the robot arrives at the target patient, the processor 101 functions as the task function switching function unit 113, and acquires task function setting contents set for the corresponding patient from the robot control server 2 via the access point 4 by the communication interface 104 (step S105). This is processing for transmitting a task function acquisition request including a patient name specifying the patient to the task function/measurement data management unit 22 of the robot control server 2, receiving the task function setting content returned from the task function/measurement data management unit 22 by the communication interface 104, and storing the content in the temporary storage unit 1033 of the data memory 103.

That is, as illustrated in FIG. 12, in a case where the processor 201 of the robot control server 2 determines that the task function acquisition request is received in the step S203 (YES in step S203), the processor 201 returns the task function setting content of the patient to the remote-controlled robot 1 of the request source by a communication interface 204 (step S208). That is, the processor 201 specifies the task function setting table 24 corresponding to the patient name included in the task function acquisition request from among the task function setting tables 24 of the plurality of patients stored in the task function setting storage unit 2032, reads out the contents, and transmits the contents to the remote-controlled robot 1. Next, the processor 201 shifts to the processing in step S201 described above.

Returning to FIG. 13, if the processor 101 of the remote-controlled robot 1 acquires the task function setting content in the step S105, the processor 101 determines whether all the task functions in the task function setting content stored in the temporary storage unit 1033 are executed, that is, it is determined whether the task for the patient has been completed (step S106). In a case where it is determined that the task is not ended yet (NO in step S106), the processor 101 functions as the manual operation notification function unit 114, and determines whether [Automatic] is set as an automatic/manual flag for the task function to be executed from now (step S107). That is, the processor 101 determines whether the remote-controlled robot 1 has reached the timing of executing switching from autonomous control to manual control.

(3-1) Execution of Automatic Task Function

In a case where it is determined that [Automatic] is set (YES in step S107), the processor 101 functions as the set task function unit set among the plurality of task function units 121, 122, . . . in the function unit storage unit 12, for example, the task function unit 121 for performing a task function [Room Temperature Measurement] of a task number [001] to automatically execute measurement (step S108).

Then, the processor 101 functions as the transmission/reception function unit 131, and transmits measurement information including a patient name, a task function, and a measurement result to the robot control server 2 via the access point 4 by the communication interface 104 (step S109). Next, the processor 101 shifts to the processing in step S106 described above.

As illustrated in FIG. 12, in a case where it is determined that the measurement information is received in the step S204 (YES in step S204), the processor 201 of the robot control server 2 stores the measurement information (step S209). That is, the processor 201 records the measurement result in the corresponding task function of the measurement recording table 25 corresponding to the patient name in the received measurement information from among the measurement recording table 25 of the plurality of patients stored in the measurement record storage unit 2033. Next, the processor 201 shifts to the processing in step S201 described above.

In this manner, for example, the remote-controlled robot 1 having the robot number [R01] arriving at the room 101 refers to the task function setting contents of the task function setting table 24 for the patient A in the robot control server 2, and starts the task function [Room Temperature Measurement] of the task number [001]. Since the task number [001] is described as [Automatic] in the task function setting table 24 for the patient A, the remote-controlled robot 1 having the robot number [R01] moves a room temperature measuring function as the task function unit 121 as it is, measures the room temperature, and transmits the result to the robot control server 2. Then, the robot control server 2 receiving the measurement result from the remote-controlled robot 1 having the robot number [R01] records the result in a measurement recording table 25 for the patient A.

Thereafter, by repeating the processing from the step S106 again, the remote-controlled robot 1 having the robot number [R01] starts the task function [Body Temperature Measurement] of the next task number [002]. Since the task number [002] of the task function setting table 24 for the patient A is also described as [Automatic], the remote-controlled robot 1 having the robot number [R01] also moves a body temperature measuring function as the task function unit 122 to measure the body temperature of the patient A, the result is transmitted to the robot control server 2. Then, the robot control server 2 receiving the measurement result from the remote-controlled robot 1 having the robot number [R01] records the result in the measurement recording table 25 for the patient A.

(3-2) Execution of Manual/Automatic Task Function

In a case where it is determined that [Automatic] is not set in the step S107, that is, [Manual] is set (NO in step S107), the processor 101 functions as the task function switching function unit 113 and determines whether control by the robot control terminal 3 has already been switched (step S110). In a case where it is determined that the control by the robot control terminal 3 is not switched yet (NO in step S110), the processor 101 functions as the call function unit 141 and calls the robot control terminal 3 via the access point 4 by the communication interface 104 (step S111). At this time, the processor 101 calls a specific terminal out of the plurality of robot control terminals 3 based on information for specifying the robot control terminal 3 for manually controlling the remote-controlled robot 1 stored in the control terminal information storage unit 1032. The robot control terminal 3 to be called is not limited to one. Then, the processor 101 determines whether there is a response from the robot control terminal 3 (step S112). In a case where it is determined that there is no response (NO in step S112), the processor 101 continues the processing of the step S111. Thus, the response from the robot control terminal 3 is waited.

As illustrated in FIG. 11, in a case where the processor 301 of the robot control terminal 3 determines that there is a call from the remote-controlled robot 1 in the step S302 (YES in step S302), the processor 301 functions as a call reception function unit 321 and notifies a nurse of the call (step S305). This notification can be made by the monitor 342 and the speaker 345 connected to the input/output interface 305. Then, the processor 301 determines whether a response operation of the nurse is performed (step S306). In a case where it is determined that there is no response operation (NO in step S306), the processor 301 continues the processing of the step S306. Thus, the response operation from the nurse is waited. The response operation is not limited to the operation of the keyboard/mouse 341 connected to the input/output interface 305, but may include a predetermined keyword voice of the nurse acquired by the microphone 344, a predetermined gesture of the nurse acquired by the camera 343, and the like.

In a case where it is determined that the nurse has operated the response (YES in step S306), the processor 301 transmits the response to the remote-controlled robot 1 of the calling source by the communication interface 304 (step S307).

Returning to FIG. 13, the processor 101 of the remote-controlled robot 1 functions as the task function switching function unit 113 to switch to control by the robot control terminal 3 (step S113) in a case where it is determined that there is a response in the step S112 (YES in step S112). Thereafter, the processor 101 transmits the contents of the task to be executed by the manual operation to the robot control terminal 3 via the access point 4 by the communication interface 104 (step S114). Then, the processor 101 determines whether the remote operation content is received from the robot control terminal 3 via the access point 4 by the communication interface 104 (step S115). When it is determined that the remote operation content is not received (NO in step S115), the processor 101 continues the processing of the step S115. Thus, the nurse waits for remote operation.

As illustrated in FIG. 11, the processor 301 of the robot control terminal 3 transmits the response to the remote-controlled robot 1 in step S307 described above, and then notifies the nurse of the task content of the task content transmitted from the remote-controlled robot 1 using the monitor 342 connected to the input/output interface 305 (step S308). Here, the processor 301 determines whether the transmitted task content is remote operation end (step S309).

In a case where the task content is not the remote operation end, the nurse who has confirmed the notification of the task content performs an operation corresponding to the task content. In other words, when the simple arm portion 181, the drive unit 182, and the camera 171 of the remote-controlled robot 1 are remotely operated, the nurse operates the operation device 346. In addition, in the case of making an interview of a patient, the monitor 342, the camera 343, the microphone 344, and the speaker 345 on the robot control terminal 3 side with respect to the camera 171, the monitor 172, the microphone 173 and the speaker 174 of the remote-controlled robot 1 are operated.

Therefore, in a case where it is determined that the remote operation is not ended (NO in step S309), the processor 101 functions as the robot operation function unit 33 or the video/audio communication function unit 142, and receives and acquires the operation contents of the operation device 346 or the monitor 342 connected to the input/output interface 305, the camera 343, the microphone 344, and the speaker 345 (step S310). Then, the processor 301 transmits the acquired operation content to the remote-controlled robot 1 by the communication interface 304 (step S311). Further, the processor 301 determines whether the acquired operation content is an interview (step S312). In a case where it is determined that it is not the interview (NO in step S312), the processor 101 shifts to the processing of step S308 described above.

Returning to FIG. 13, when it is determined that the remote operation content is received from the robot control terminal 3 in the step S115 (YES in step S115), the processor 101 of the remote-controlled robot 1 functions as the robot drive control unit 15 to execute the remote operation content (step S116). That is, the processor 101 drives the simple arm portion 181 and the drive unit 182 connected to the mechanical unit interface 107 according to the received remote control contents. Then, the processor 101 determines whether transmission of the measurement result to the robot control server 2 is necessary as the result of the remote operation (step S117). In a case where it is determined that transmission to the robot control server 2 is necessary (YES in step S117), the processor 101 shifts to the processing of step S109 described above. Then, the processor transmits the measurement result to the robot control server 2 in step S109 described above, and shifts the processing of step S106 described above.

For example, when the remote-controlled robot 1 having the robot number [R01] starts the task function [Blood Pressure Measurement] having the task number [003] by referring to the task function setting contents of the task function setting table 24 for the patient A in the robot control server 2, the task number [003] is described as [Manual] in the task function setting table 24 for the patient A. In this case, the remote-controlled robot 1 switches the control of the function from autonomous control to manual control, and calls a nurse on the robot control terminal 3 side. After responding of the nurse by the robot control terminal 3, the robot notifies the nurse of the arrival of the order of blood pressure measurement as a task content to be performed by manual control, the control right of the remote-controlled robot 1 having the robot number [R01] is transferred to the robot control terminal 3. A nurse operates the simple arm portion 181, the camera 171, the drive unit 182, or the like of the remote-controlled robot 1 having the robot number [R01] by the robot operation function unit 33 of the robot control terminal 3, the blood pressure monitor 6 is mounted on the arm of the patient A to measure the blood pressure. Since the blood pressure monitor 6 has a communication function with the remote-controlled robot 1, the measurement result is transmitted from the remote-controlled robot 1 to the robot control server 2, and the robot control server 2 records the result in the measurement recording table 25 for the patient A.

Further, as illustrated in FIG. 11, the processor 301 of the robot control terminal 3 functions as the patrol prediction/task setting unit 31 in a case where it is determined that the interview is made in step S312 described above (YES in step S312), and receives the input operation of the interview contents by the keyboard/mouse 341 (step S313). Then, the processor 101 transmits the interview contents to the robot control server 2 by the communication interface 304 (step S314). Next, the processor 301 shifts to the processing in step S308 described above.

As illustrated in FIG. 12, in a case where it is determined that the interview content is received in the step S205 (YES in step S205), the processor 201 of the robot control server 2 functions as the task function/measurement data management unit 22, and stores the received interview content in the interview content storage unit 26 of the interview storage unit 2034 (step S210). Next, the processor 201 shifts to the processing in step S201 described above.

For example, when a task to be executed next is a task function [Interview] of a task number [004] in the task function setting table 24 for the patient A, a nurse uses a videophone function of the robot control terminal 3, performs the interview with the patient A via the videophone function unit 14 on the remote-controlled robot 1 side having the robot number [R01], and inputs the interview contents by the keyboard/mouse 341. The input content is transmitted to the robot control server 2, and the robot control server 2 separately saves the input content as an interview record for the patient A.

(4) Movement to Next Room

As described above, the processor 101 of the remote-controlled robot 1 sequentially executes the task contents acquired from the task function setting table 24 by autonomous control or manual control. In a case where it is determined that the task for the patient has ended in step S106 described above in FIG. 13 (YES in step S106), the processor 101 shifts to the processing of step S103 described above. In this case, although not illustrated in particular, the processor 101 transmits the task contents of the end of the remote operation to the robot control terminal 3.

Then, in step S103 described above, the processor 101 confirms the next patrol order from the patrol schedule stored in the temporary storage unit 1033, and if [Completion] is not set in the patrol order to be executed from now, the processor shifts to the processing of step S104 and moves the robot to the next patient.

For example, the remote-controlled robot 1 having the robot number [R01] determines that the task content for the patient A is completed when all the tasks listed in the task function setting table 24 for the patient A are completed, and goes to the patrol task of a patient B in a room 102 which is Patrol Order 2 of the patrol schedule table, the task contents are executed based on the task function setting table 24 for the patient B.

(5) End of Patrol Task

Then, in a case where it is determined that [Completion] is set in step S103 described above (YES in step S103), since it is the fact that the robot for all patients to be patrolled has been patrolled, the processor 101 shifts to the processing of step S101 described above.

Thus, when the patrol order of the patrol schedule table for the remote-controlled robot 1 is ended, the patrol task is ended. In this case, the processor 101 may function as the drive unit control function unit 152 to move the remote-controlled robot 1 to a predetermined standby place by the drive unit 182.

In the first embodiment as described above, the remote-controlled robot 1 autonomously travels to a plurality of task execution places such as a sickroom according to a patrol schedule and executes a plurality of tasks at each task execution place, and includes the task function switching function unit 113 which can be provided by the processor 101. The task function switching function unit 113 operates as a setting acquisition unit and acquires setting of whether to perform an autonomous operation or to perform a manual operation by the operation of an operator such as a nurse from the remote control terminal for each of the plurality of tasks to be executed at each task execution place listed in the task function setting table 24 from the robot control server 2. In addition, the task function switching function unit 113 operates as a first switching unit, and switches between task execution by autonomous operation and task execution by manual operation based on the acquired setting.

Thus, according to the first embodiment, the remote-controlled robot 1 is made to automatically perform the task autonomously performed by the remote-controlled robot 1, and only the task manually performed by an operator such as a nurse can be manually performed from a remote place, and even for a facility where the autonomous control direction task and the manual control direction task are mixed. Thus, the remote-controlled robot 1 can be introduced, and the efficiency of task by the remote-controlled robot 1 can be improved.

In a first embodiment, the remote-controlled robot control system includes the remote-controlled robot 1 which autonomously travels to a plurality of task execution places such as a sickroom according to a patrol schedule and executes a plurality of tasks at each task execution place, the robot control terminal 3 for manually operating the remote-controlled robot 1, and the robot control server 2 to which the remote-controlled robot 1 and the robot control terminal 3 are accessed. The robot control server 2 includes the patrol schedule table 23 as a schedule storage unit for storing a patrol schedule, and the task function setting table 24 as a task storage unit for storing settings of whether to perform autonomous operation or to perform manual operation by the operation of an operator such as a nurse from the robot control terminal 3 for each of a plurality of tasks to be executed at the task execution places relating to each of the plurality of task execution places. In addition, the robot control terminal 3 includes the patrol prediction/task setting unit 31 which can be provided by the processor 101. The patrol prediction/task setting unit 31 operates as a pre-set unit, and performs setting of a patrol schedule and setting of each of a plurality of tasks in the robot control server 2 prior to the operation start of the remote-controlled robot 1. The remote-controlled robot 1 includes the task function switching function unit 113 which can be provided by the processor 101. The task function switching function unit 113 operates as a setting acquisition unit, and acquires setting for each of the patrol schedule and the plurality of task from the robot control server 2. In addition, the task function switching function unit 113 operates as the first switching unit, and switches between task execution by autonomous operation and task execution by manual operation based on the acquired setting.

In this way, the task suitable for automation is autonomously controlled, and also the direct temperature detection of the patient, the measurement of blood pressure, or manual control of a task suitable for manual control such as an interview is set in the task function setting table 24 in advance, the remote-controlled robot 1 performs the task in order based on a state set in the task function setting table 24, calls a remote operator when the order of the manual control task comes, the function is switched to manual operation, and only the task to be manually performed is manually performed by an operator from a remote place. Thus, the remote-controlled robot 1 can be utilized in a facility where autonomous control direction task and manual control direction task coexist.

Second Embodiment

Next, a second embodiment of the present invention will be described. The present embodiment is adapted to cope with a case where a patient to be measured is sleeping during a patrol. The same configurations as those of the first embodiment are denoted by the same reference numerals as those of the first embodiment and description thereof will be appropriately omitted.

Figure 14:
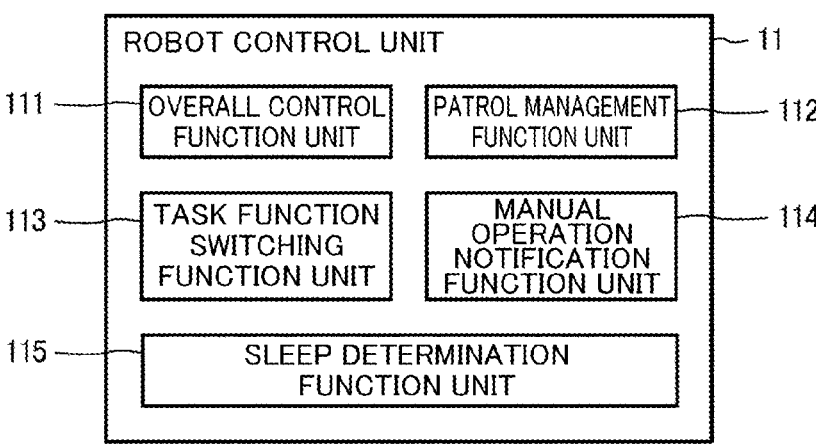
FIG. 14 is a block diagram illustrating an example of a functional configuration of a robot control unit in a remote-controlled robot according to a second embodiment of the present invention.

FIG. 14 is a diagram illustrating an example of a functional configuration of the robot control unit 11 in the remote-controlled robot 1 according to the second embodiment. The robot control unit 11 in the present embodiment includes a sleep determination function unit 115 in addition to the configuration in the first embodiment. The sleep determination function unit 115 has a function of automatically checking the state of the patient to be measured before execution of the task function and determining whether the patient is sleeping or waking up. Whether the user is sleeping can be determined in a complex manner based on an image of the patient imaged by the camera 171, a voice of the patient acquired by the microphone 173, and the like. For example, from the image, information of the patient lying on a bed, the closed eyes, the numerical representation of the vital sign monitor, or the like can be acquired, and a specific pattern seen during sleep such as sleeping breath and snoring can be acquired from the voice.

FIG. 15 is a diagram illustrating an example of the contents of the task function setting table 24 created in the robot control server 2 in the second embodiment in units of patients. In the present embodiment, the task function setting table 24 includes option flags 1 and 2 in addition to items similar to those in the first embodiment. These option flags are set at [*]. The option flag 1 is set to indicate that when the patient has worked, the automatic execution target function can be switched to manual execution. When the option flag 2 is set to indicate that the content of the task can be skipped in a case where the execution of the manual task is not suitable, for example, in a case where the patient is sleeping.

FIG. 16 is a diagram illustrating an example of the contents of the measurement recording table 25 created in the robot control server 2 in the second embodiment in units of patients. In a case where the patient is sleeping, for example, [sleep] indicating that the patient is sleeping is entered in the remark item. For the result of the task which has not been executed, a symbol indicating the result, for example, [-], is entered.

Figure 17:
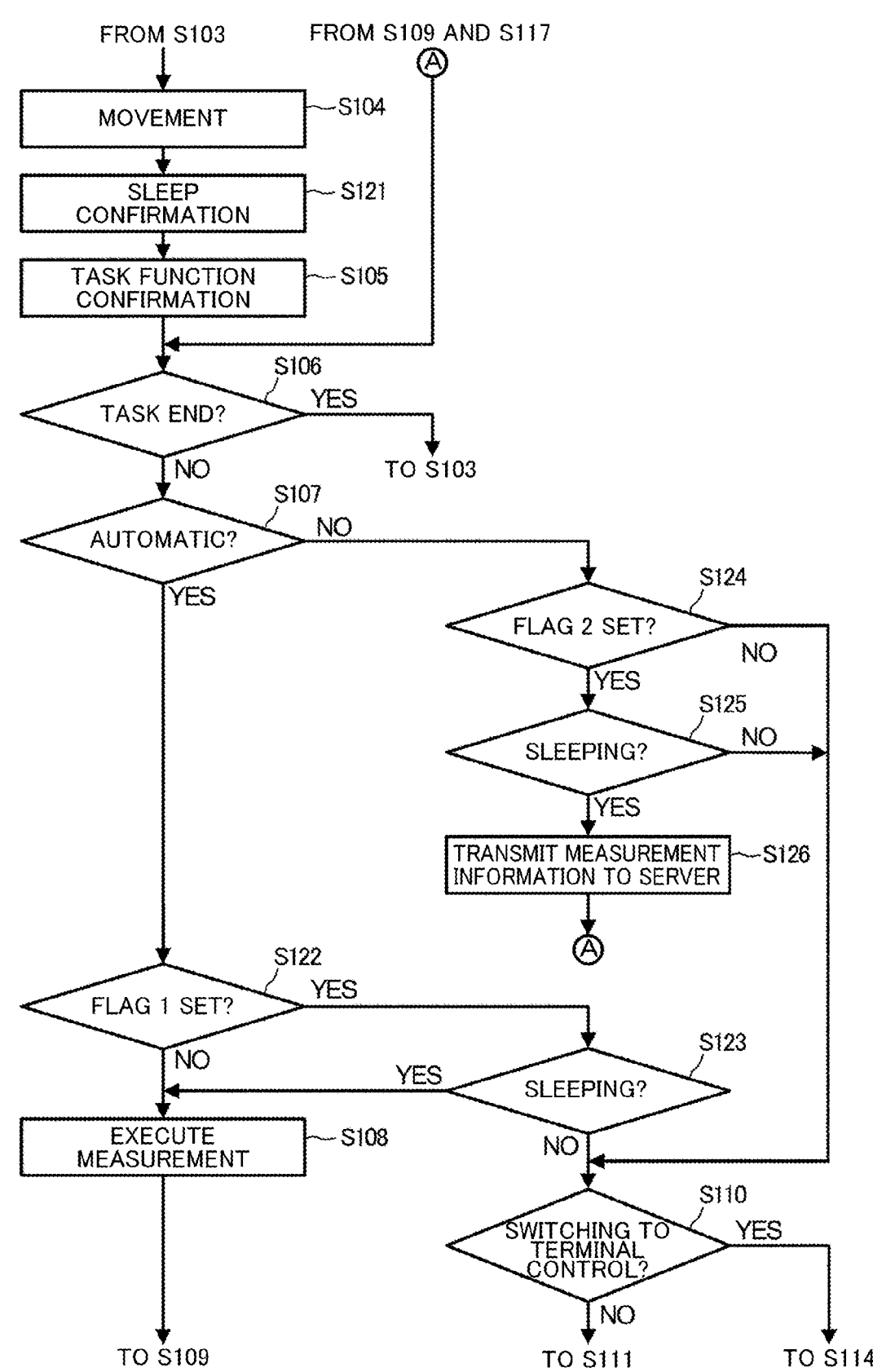
FIG. 17 is a flowchart illustrating an example of an operation of the remote-controlled robot according to the second embodiment.

FIG. 17 is a flowchart illustrating an example of an operation of the remote-controlled robot 1 according to the second embodiment. In the same drawing, parts similar to those of the first embodiment are omitted.

When moving the robot to the patient in step S104 described above, the processor 101 of the remote-controlled robot 1 functions as the sleep determination function unit 115 to check the state of the patient, confirms whether the patient to be measured is sleeping, and stores the confirmation result in the temporary storage unit 1033 (step S121).

Thereafter, the processor 101 acquires the task function setting contents set for the corresponding patient from the robot control server 2 in step S105 described above, and determines whether the task for the patient has ended in step S106 described above. In a case where the task is not ended yet, it is determined whether [Automatic] is set as an automatic/manual flag in step S107.

Here, in a case where it is determined that [Automatic] is set (YES in step S107), in the present embodiment, the processor 101 functions as the sleep determination function unit 115, it is determined whether the option flag 1 is set to a task function to be executed from now (step S122). In a case where it is determined that the option flag 1 is not set (NO in step S122), the processing is shifted to the processing of the step S108 and the measurement is automatically executed.

On the other hand, in a case where it is determined that the option flag 1 is set (YES in step S122), the processor 101 functions as the sleep determination function unit 115 to determine whether the patient is sleeping (step S123). In this determination, a confirmation result of whether the user is sleeping, which is stored in the temporary storage unit 1033, can be used. In a case where it is determined that the user is sleeping (YES in step S123), the processor 101 shifts to the processing of step S108 described above and automatically executes the measurement.

On the other hand, in a case where it is determined that the patient is not sleeping (NO in step S123), the processor 101 shifts to the processing of step S110 described above. That is, the manual execution is switched even if it is an automatic execution target function.

In addition, in a case where it is determined that [Automatic] is not set in step S107 described above, that is, [Manual] is set (NO in step S107), in the present embodiment, the processor 101 functions as the sleep determination function unit 115 to determine whether the option flag 2 is set to a task function to be executed from now (step S124). Here, in a case where it is determined that the option flag 2 is not set (NO in step S124), the processor shifts to the processing of step S110 described above.

On the other hand, in a case where it is determined that the option flag 2 is set (YES in step S124), the processor 101 determines whether the patient is sleeping (step S125). In this determination, a confirmation result of whether the user is sleeping, which is stored in the temporary storage unit 1033, can be used. In a case where it is determined that the user is not sleeping (NO in step S125), the processor 101 shifts to the processing of step S110 described above.

In addition, in a case where it is determined that the patient is sleeping (YES in step S125), the processor 101 transmits measurement information including a patient name, a task function, and a measurement result to the robot control server 2 via the access point 4 by the communication interface 104 (step S126). In this case, the measurement result indicates that the task has not been executed. Next, the processor 101 shifts to the processing in step S106 described above. In the robot control server 2 receiving such measurement information, [-] is recorded in the corresponding measurement item of the measurement recording table 25 for the corresponding patient, and [sleep] indicating that the patient is sleeping is recorded in the remark item.

As described above, in the second embodiment, a plurality of tasks to be executed at each task execution place, such as a sickroom, are tasks to be executed on a task execution target person, such as a hospitalized patient. For each of a plurality of tasks to be executed at each task execution place, the task function switching function unit 113, as the setting acquisition unit, further acquires a setting indicating whether the task listed as the option flag 2 in the task function setting table 24 can be executed during sleep. In addition, the remote-controlled robot 1 also includes a sleep determination function unit 115 that can be provided by the processor

101. The sleep determination function unit 115 operates as a sleep state detection unit, and detects whether the task execution target person is sleeping. Further, the sleep determination function unit 115 operates as a selection unit, and in a case where it is detected that the task execution target person is sleeping, based on the setting acquired by the task function switching function unit 113, the task execution target person selects and executes a task that can be executed during sleep.

Therefore, according to the second embodiment, the same operation and effect as those of the first embodiment can be achieved, and only such a task that does not cause the task execution target person can be performed, and the sleep of the task execution target person can be prevented from being disturbed.

Further, according to the second embodiment, the sleep determination function unit 115 operates as a measurement information recording unit, and records that the task execution target person was asleep and that which task cannot be performed for this reason in a measurement recording table of the robot control server 2. An operator such as a nurse who has confirmed the table can execute the task which cannot be executed by himself or herself, can incorporate it into the patrol schedule of the remote-controlled robot 1 again, and can execute the task by the remote-controlled robot 1 after the lapse of time.

Third Embodiment

Next, a third embodiment of the present invention will be described. The present embodiment is adapted to cope with the case where a patient to be measured is absent for a reason of a toilet or the like during a patrol. The same configurations as those of the first embodiment are denoted by the same reference numerals as those of the first embodiment and description thereof will be appropriately omitted.

Figure 18:
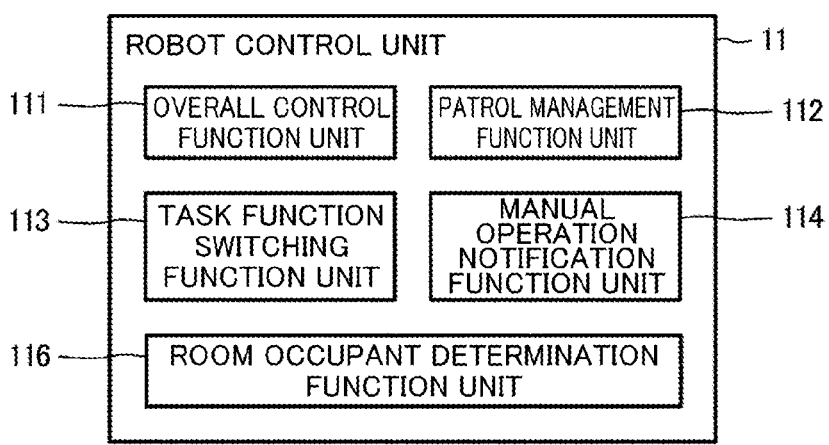
FIG. 18 is a block diagram illustrating an example of a functional configuration of a robot control unit in a remote-controlled robot according to a third embodiment of the present invention.

FIG. 18 is a block diagram illustrating an example of a functional configuration of the robot control unit 11 in the remote-controlled robot 1 according to the third embodiment. The robot control unit 11 of the present embodiment includes a room occupant determination function unit 116 in addition to the configuration of the first embodiment. The room occupant determination function unit 116 has a function of determining whether a patient to be measured is in a room before execution of the task function, and correcting a patrol schedule in the robot control server 2 in a case where the patient is absent. Whether the patient is in the room or not can be determined based on the image of the inside of the sickroom imaged by the camera 171.

Figure 19:
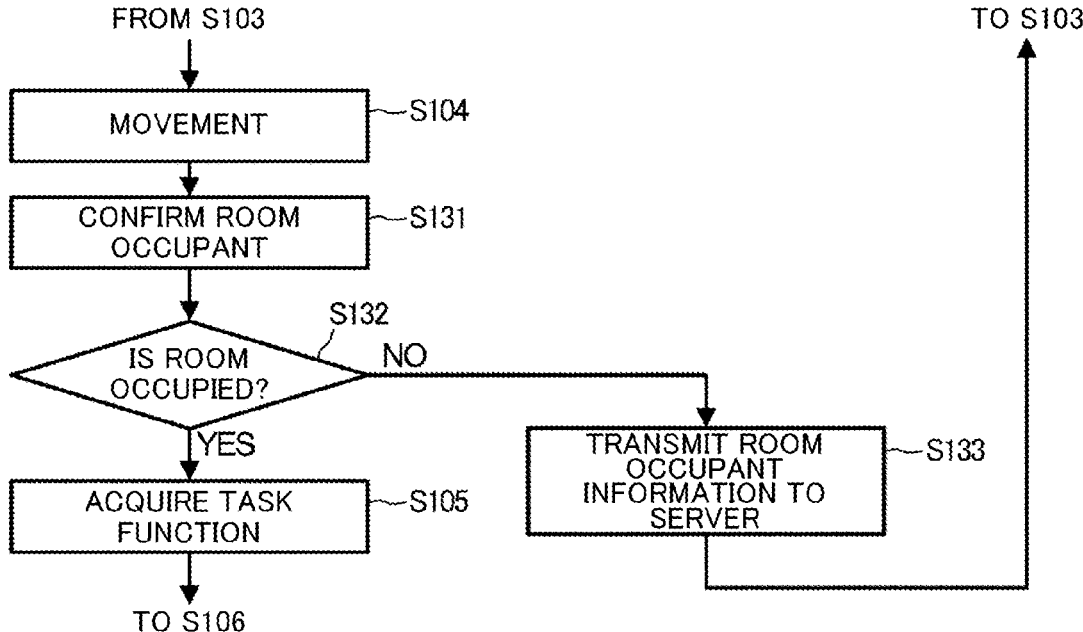
FIG. 19 is a flowchart illustrating an example of an operation of the remote-controlled robot according to the third embodiment.

FIG. 19 is a flowchart illustrating an example of an operation of the remote-controlled robot 1 according to the third embodiment. In the same drawing, parts similar to those of the first embodiment are omitted.

When the robot moves to the patient in step S104 described above, the processor 101 of the remote-controlled robot 1 functions as the room occupant determination function unit 116, confirms whether the patient to be measured is present in the room, and stores the confirmation result in the temporary storage unit 1033 (step S131).

Then, the processor 101 determines whether the patient is in the room (step S132). In a case where it is determined that the patient is in the room (YES in step S132), the processor 101 shifts to the processing of step S105 described above, and acquires the task function setting content set for the corresponding patient from the robot control server 2.

On the other hand, in a case where it is determined that the patient is not in the room, that is, is absent (NO in step

S132), the processor 101 transmits the room occupant information to the robot control server 2 via the access point 4 by the communication interface 104 (step S133). The room occupant information includes information specifying a patient who has been absent, for example, a patient name. Next, the processor 101 shifts to the processing in step S103 described above. That is, the processor 101 skips the task for the patient who is absent, and moves to the patrol task for the next patient.

Figure 20:
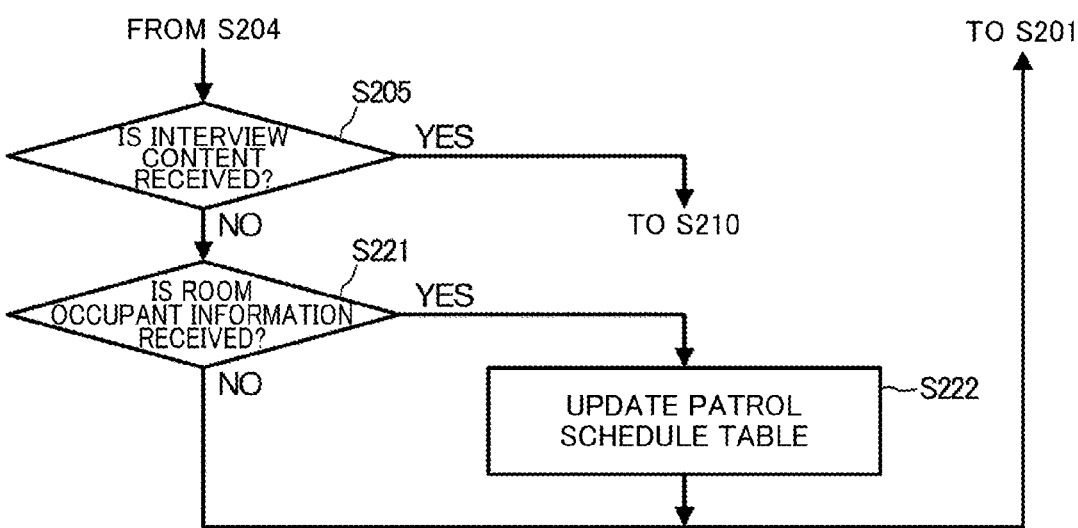
FIG. 20 is a flowchart illustrating an example of an operation of a robot control server in the third embodiment.

FIG. 20 is a flowchart illustrating an example of the operation of the robot control server 2 in the third embodiment. In the same drawing, parts similar to those of the first embodiment are omitted.

In a case where the processor 201 of the robot control server 2 determines that the interview content is not received in step S205 described above (NO in step S205), the processor 201 further functions as the patrol prediction management unit 21 to determine whether room occupant information is received from the remote-controlled robot 1 by the communication interface 204 (step S221). In a case where it is determined that the room occupant information is not received (NO in step S221), the processor 201 shifts to the processing of step S201 described above.

On the other hand, in a case where it is determined that the room occupant information is received (YES in step S222), the processor 201 updates the patrol schedule table 23 stored in the patrol schedule storage unit 2031 (step S222). Next, the processor 201 shifts to the processing in step S201 described above.

Figure 21:
FIG. 21 is a diagram illustrating an example of a content of a patrol schedule table updated by update processing of a patrol schedule table in FIG. 20.

FIG. 21 is a diagram illustrating an example of the contents of the patrol schedule table 23 updated by the update processing of the patrol schedule table 23 in the step S222. For example, it is assumed that room occupant information indicating that the patient A to be measured is absent is received from the remote-controlled robot 1 having the robot number [R01]. In this case, the processor 101 functioning as the patrol prediction management unit 21 rewrites the description of the end of the patrol order of the remote-controlled robot 1 in the patrol schedule table 23, in this case, the description of the items of the patrol order 4 from [Completion] to [101: A] indicating the corresponding patient A. Further, the processor 201 shifts the end of the patrol schedule table 23 by one line, that is, adds items of the patrol order 5, and describes [Completion]. By updating the patrol schedule table 23 in this way, the remote-controlled robot 1 having the robot number [R01] can be made to finally patrol again to the place of the patient who is absent.

As described above, in the third embodiment, a plurality of tasks to be executed at each task execution place such as a sickroom are tasks to be executed to a task execution target person such as a hospitalized patient, the remote-controlled robot 1 further includes the room occupant determination function unit 116 that may be provided by the processor 101. The room occupant determination function unit 116 operates as an absence detection unit and detects whether a task execution target person is absent. Further, the room occupant determination function unit 116 operates as a correction unit, and corrects the patrol schedule of the remote-controlled robot 1 indicated by the patrol schedule table 23 in the robot control server 2 in a case where it is detected that the task execution target person is absent.

Therefore, according to the third embodiment, the same action and effect as those of the first embodiment can be achieved, and in a case where the task execution target person is absent, the patrol schedule is automatically rearranged. Thus, it is possible to execute the task for the task execution target person again thereafter.

Fourth Embodiment

Next, a fourth embodiment of the present invention will be described. In the present embodiment, the nurse is identified and automatic/manual operation can be switched according to the skill level of the nurse. The same configurations as those of the first embodiment are denoted by the same reference numerals as those of the first embodiment and description thereof will be appropriately omitted.

Figure 22:
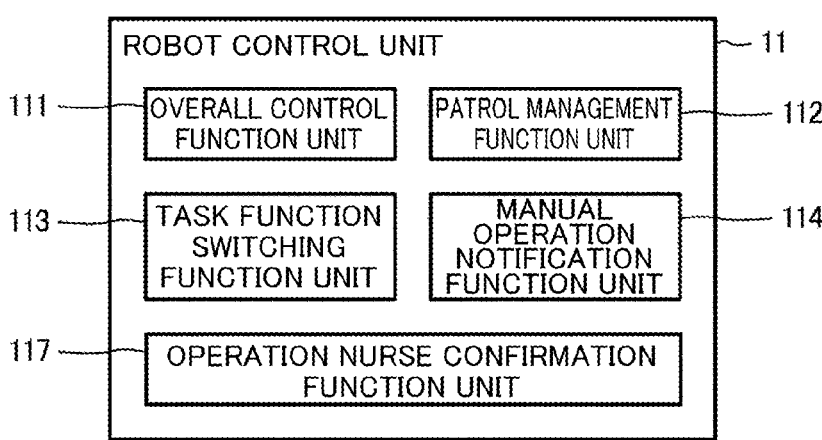
FIG. 22 is a block diagram illustrating an example of a functional configuration of a robot control unit in a remote-controlled robot according to a fourth embodiment of the present invention.

FIG. 22 is a block diagram illustrating an example of a functional configuration of the robot control unit 11 in the remote-controlled robot 1 according to the fourth embodiment. The robot control unit 11 of the present embodiment includes an operation nurse confirmation function unit 117 in addition to the configuration of the first embodiment. The operation nurse confirmation function unit 117 has a function of confirming the skill level of a nurse who is trying to remotely operate the remote-controlled robot 1 from the robot control terminal 3.

Figure 23:
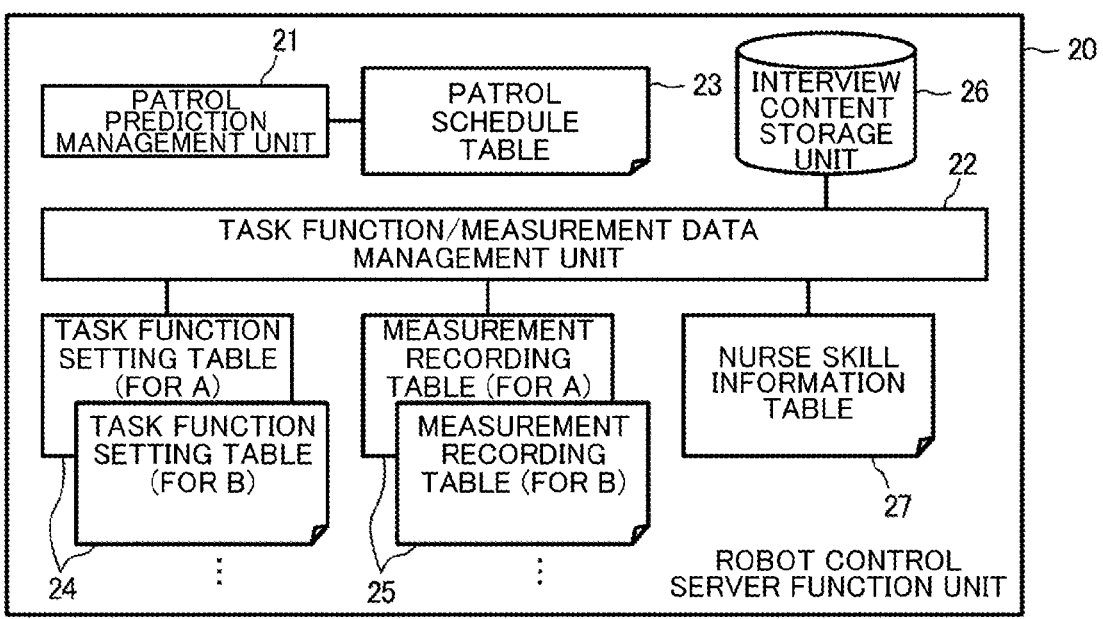
FIG. 23 is a diagram illustrating an example of a functional configuration of a robot control server in the fourth embodiment.

FIG. 23 is a block diagram illustrating an example of a functional configuration of the robot control server 2 in the fourth embodiment. In the robot control server 2 in the present embodiment, in addition to the configuration of the first embodiment, a nurse skill information table 27 is connected to the task function/measurement data management unit 22. The storage area of the nurse skill information table 27 can be secured in the data memory 203.

In addition, in the present embodiment, it is assumed that the item of the option flag 1 as described in the third embodiment is included in the task function setting table 24.

FIG. 24 is a diagram illustrating an example of a content of the nurse skill information table 27. In the nurse skill information table 27, the skill level of each nurse is described in association with a nurse number identifying each nurse. Here, the nurse skill indicates the operation capability of the remote-controlled robot 1 using the robot control terminal 3, and does not mean the capability of nurse task as a nurse.

Figure 25:
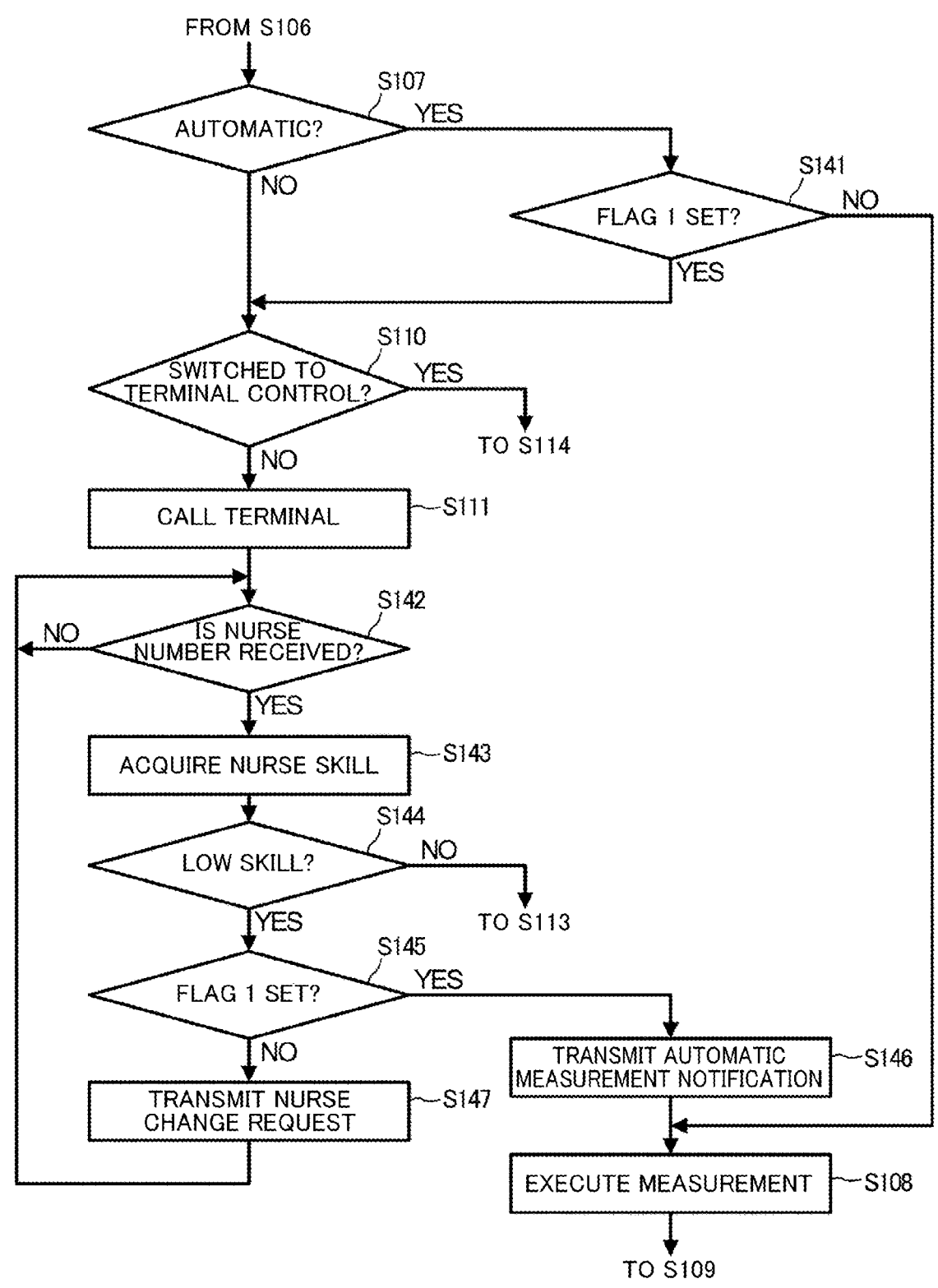
FIG. 25 is a flowchart illustrating an example of an operation of the remote-controlled robot according to the fourth embodiment.

FIG. 25 is a flowchart illustrating an example of an operation of the remote-controlled robot 1 according to the fourth embodiment. In the same drawing, parts similar to those of the first embodiment are omitted.

In a case where it is determined that [Automatic] is set as an automatic/manual flag in step S107 described above (YES in step S107), the processor 101 functions as the operation nurse confirmation function unit 117 and determines whether the option flag 1 is set to a task function to be executed from now (step S141). In a case where it is determined that the option flag 1 is not set (NO in step S141), the process shifts to the processing of step S108 described above and automatically executes the measurement.

On the other hand, in a case where it is determined that the option flag 1 is set (YES in step S141), the processor 101 determines whether the control has been switched to the control by the robot control terminal 3 in step S110 described above, and when it is determined that the control has been switched to the control by the robot control terminal 3 yet, in step S111 described above, the robot control terminal 3 is called through the access point 4 by the communication interface 104.

In the present embodiment, the processor 101 determines whether the nurse number is received from the robot control terminal 3 by the communication interface 104 (step S142). In a case where it is determined that the nurse number is not received (NO in step S142), the processor 101 continues the processing of the step S142. Thus, the robot control terminal 3 waits for the nurse number to be transmitted.

Figure 26:
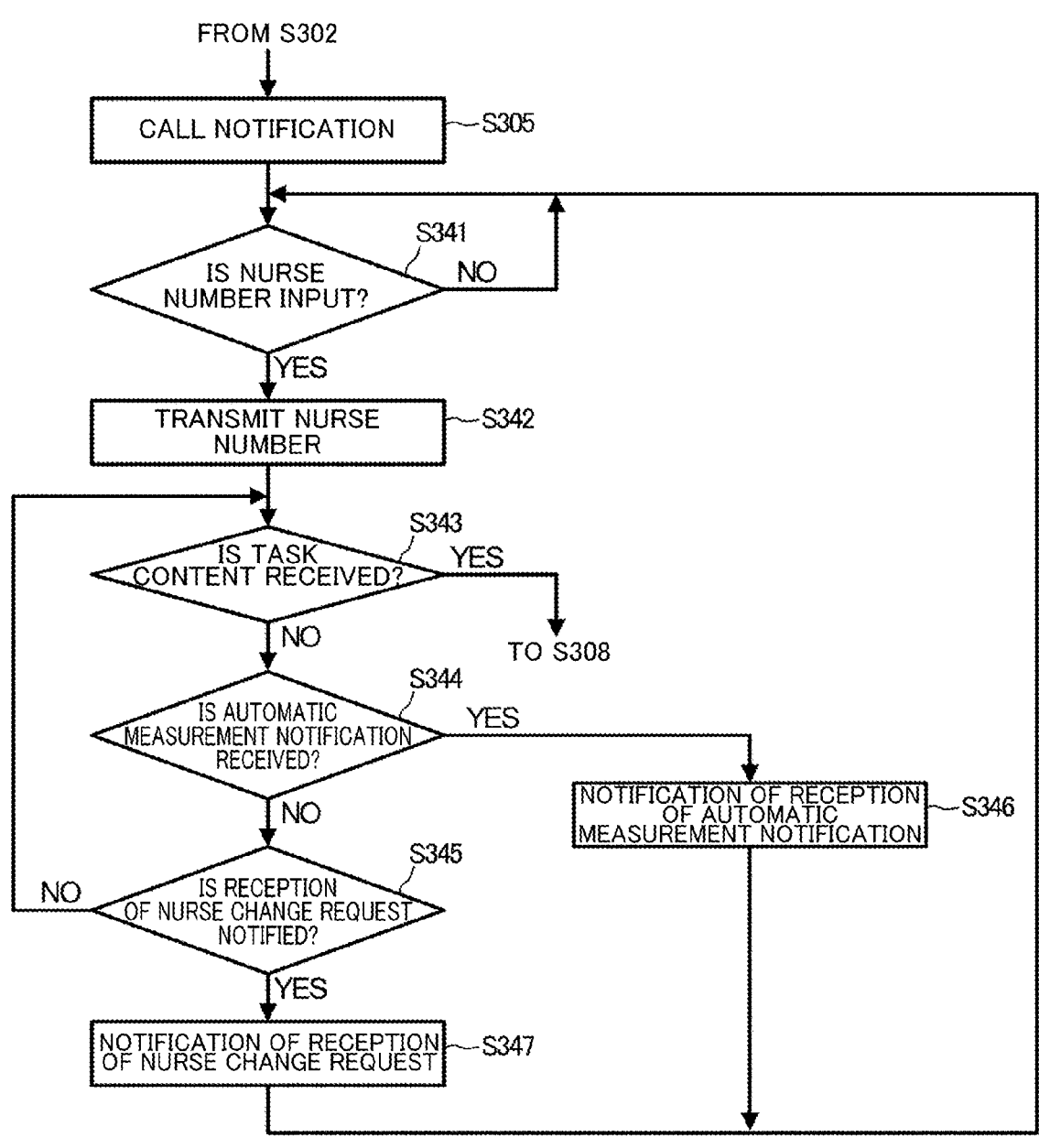
FIG. 26 is a flowchart illustrating an example of an operation of a robot control terminal in the fourth embodiment.

FIG. 26 is a flowchart illustrating an example of an operation of the robot control terminal 3 in the fourth embodiment. In the same drawing, parts similar to those of the first embodiment are omitted.

After the processor 301 of the robot control terminal 3 notifies the nurse of the call in step S305 described above, in the present embodiment, the processor 301 determines whether there is an input operation of the nurse number as a response operation of the nurse (step S341). In a case where it is determined that there is no input operation of the nurse number (NO in step S341), the processor 301 continues the processing of the step S341. Thus, the terminal waits for input operation of the nurse number by a nurse.

In a case where it is determined that there is the input operation of the nurse number (YES in step S341), the processor 301 transmits the input nurse number to the remote-controlled robot 1 of the calling source by the communication interface 304 (step S342).

Returning to FIG. 25, in a case where it is determined that the nurse number is received in step S142 described above (YES in step S142), the processor 101 of the remote-controlled robot 1 acquires the skill level of the nurse of the nurse number from the robot control server 2 via the access point 4 by the communication interface 104 (step S143). This is processing for transmitting a nurse skill inquiry including a nurse number to the task function/measurement data management unit 22 of the robot control server 2, receiving the nurse skill level returned from the task function/measurement data management unit 22 by the communication interface 104, and storing the level in the temporary storage unit 1033 of the data memory 103.

Figure 27:
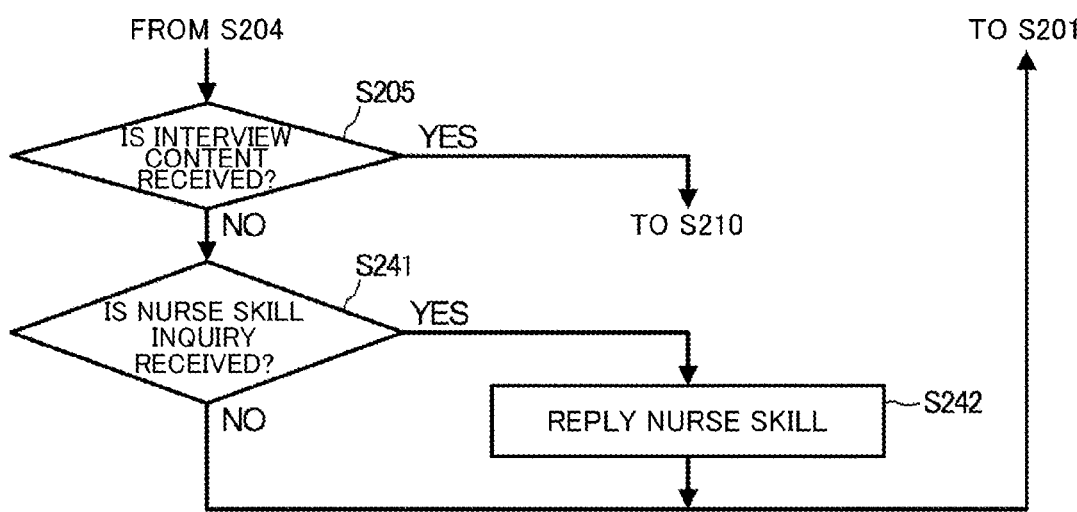
FIG. 27 is a flowchart illustrating an example of an operation of a robot control server in the fourth embodiment.

FIG. 27 is a flowchart illustrating an example of an operation of the robot control server 2 in the fourth embodiment. In the same drawing, parts similar to those of the first embodiment are omitted.

In a case where it is determined that the interview content is not received in step S205 described above (NO in step S205), the processor 201 of the robot control server 2 further determines whether a nurse skill inquiry is received from the remote-controlled robot 1 by the communication interface 204 (step S241). In a case where it is determined that the nurse skill inquiry is not received (NO in step S241), the processor 201 shifts to the processing of step S201 described above.

On the other hand, in a case where it is determined that the nurse skill inquiry has been received (YES in step S241), the nurse skill level corresponding to a nurse number included in the received nurse skill inquiry is returned by the communication interface 204 (step S242). That is, the processor 201 reads out the skill level of the nurse corresponding to the nurse number included in the nurse skill inquiry from the nurse skill information table 27, and transmits the level to the remote-controlled robot 1. Next, the processor 201 shifts to the processing in step S201 described above.

Returning to FIG. 25, if the nurse skill level is acquired in step S143 described above, the processor 101 of the remote-controlled robot 1 determines whether the skill level of the nurse is [Low Skill] (step S144). In a case where it is determined that the skill level of the nurse is not [Low Skill], that is, [High Skill] (NO in step S144), the processor 101 shifts to the processing of step S113 described above.

As illustrated in FIG. 26, the processor 301 of the robot control terminal 3 transmits the nurse number to the remote-controlled robot 1 in step S342 described above, and then determines whether the task content transmitted from the remote-controlled robot 1 is received (step S343). In a case where it is determined that the task content is not received (NO in step S343), the processor 301 further determines whether the automatic measurement notification transmitted from the remote-controlled robot 1 is received (step S344). In a case where it is determined that the automatic measurement device is not received (NO in step S344), the processor 301 further determines whether a nurse change request transmitted from the remote-controlled robot 1 is received (step S345). In a case where it is determined that the nurse change request is not received (NO in step S345), the processor 301 shifts to the processing of the step S343. Thus, the processor 301 waits for the task contents, the automatic measurement notification, or the nurse change request to be transmitted from the remote-controlled robot 1.

In a case where it is determined that the automatic measurement device is received in step S343 described above (YES in step S344), the processor 301 shifts to the processing of step S308 described above. Thus, even in the automatic execution target function, if the skill level of the nurse is [High Skill], the automatic execution is switched to manual execution.

Returning to FIG. 25, in a case where the processor 101 of the remote-controlled robot 1 determines that the skill level of the nurse is [Low Skill] in step S144 described above (YES in step S144), the processor 101 further determines whether the option flag 1 is set to a task function to be executed from now (step S145). Here, in a case where it is determined that the option flag 1 is set (YES in step S145), since the task is the task content that can be automatically executed, the processor 101 transmits an automatic measurement notification to the robot control terminal 3 via the access point 4 by the communication interface 104 (step S146). The automatic measurement notification indicates that the measurement which is the content of the function is automatically executed, and requests another nurse to change the nurse because the nurse's skill level is low. Next, the processor 101 shifts to the processing in step S108 described above and automatically executes the measurement.

As illustrated in FIG. 26, in a case where it is determined that the automatic measurement notification is received in step S344 described above (YES in step S344), the processor 301 of the robot control terminal 3 notifies a nurse of the reception of the automatic measurement notification by a monitor connected to the input/output interface 305 (step S346). That is, the remote-controlled robot 1 automatically executing the measurement and the nurse change request are displayed on the monitor 342. Next, the processor 301 shifts to the processing in step S341 described above and waits for changing the nurse.

Returning to FIG. 25, in a case where it is determined that the option flag 1 is not set in step S145 described above (NO in step S145), the processor 101 of the remote-controlled robot 1 transmits the nurse change request to the robot control terminal 3 via the access point 4 by the communication interface 104 (step S147). That is, since the fact that the option flag 1 is not set means that the task is determined later in the task requiring manual execution in step S107 described above, the processor 101 requests the robot control terminal 3 to change to a nurse having a high level of operation skill. Next, the processor 101 shifts to the processing in step S142 described above.

As illustrated in FIG. 26, in a case where it is determined that the nurse change request is received in step S345 described above (YES in step S345), the processor 301 of the robot control terminal 3 notifies the nurse of the reception of the nurse change request by a monitor connected to the input/output interface 305 (step S347). That is, the nurse change request is displayed on the monitor 342. Next, the processor 301 shifts to the processing in step S341 described above and waits for a change of nurse.

For example, in a case where the nurse having a nurse number [N002] as illustrated in FIG. 24 responds to the call notification from the remote-controlled robot 1, the nurse is a nurse with [Low Skill]. Here, when the option flag 1 is set as in the task [Body Temperature Measurement] of the task number [002] as illustrated in FIG. 15, it is possible to switch to the measurement by manual operation of the nurse, but since the level of the operation skill of the responding nurse is low, automatic measurement is performed. Then, a change to a nurse whose operation skill is high level is requested.

On the other hand, in a case where the nurse number [N001], which is [High Skill], responds to the call notification from the remote-controlled robot 1 as illustrated in FIG. 24, the measurement is switched to the measurement by manual operation of the nurse.

Here, an example of the case of two stages of high and low as the nurse skill level has been explained, but it is of course possible to have multiple stages. In this case, automatic measurement/manual measurement can be set in stages.

As described above, in the fourth embodiment, a plurality of tasks include tasks that can be operated by both autonomous operations and manual operations such as body temperature measurement, and the remote-controlled robot 1 includes the operation nurse confirmation function unit 117, which can be provided by the processor 101. The operation nurse confirmation function unit 117 operates as a level acquisition unit, and acquires an operation skill level of an operator of the remote-controlled robot 1, such as a nurse described in the nurse skill information table 27, from the robot control server 2. In addition, the operation nurse confirmation function unit 117 operates as a second switching unit, and for a task capable of both autonomous operation and manual operation, switches between the task execution by the autonomous operation and the task execution by the manual operation according to the acquired operation skill level.

Therefore, according to the fourth embodiment, the same operation and effect as those of the first embodiment can be achieved, and switching can be performed according to the operation skill level of an operator such as a nurse.

Fifth Embodiment

Next, a fifth embodiment of the present invention will be described. The present embodiment is adapted to cope with the case where an automatic analysis function of the interview contents is added. The same configurations as those of the first embodiment are denoted by the same reference numerals as those of the first embodiment and description thereof will be appropriately omitted.

Figure 28:
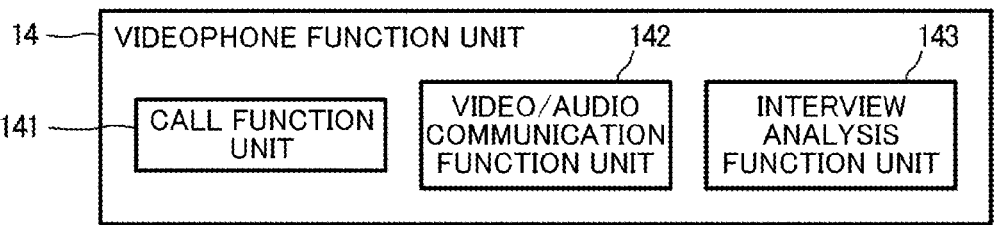
FIG. 28 is a block diagram illustrating an example of a functional configuration of a videophone function unit in a remote-controlled robot according to a fifth embodiment of the present invention.

FIG. 28 is a block diagram illustrating the functional configuration of the videophone function unit 14 of the remote-controlled robot 1 according to the fifth embodiment. In addition to the configuration of the first embodiment, the videophone function unit 14 of the present embodiment includes the interview analysis function unit 143. The interview analysis function unit 143 has a function of automatically recording and automatically analyzing the conversation contents between the patient and the nurse during the interview.

Figure 29:
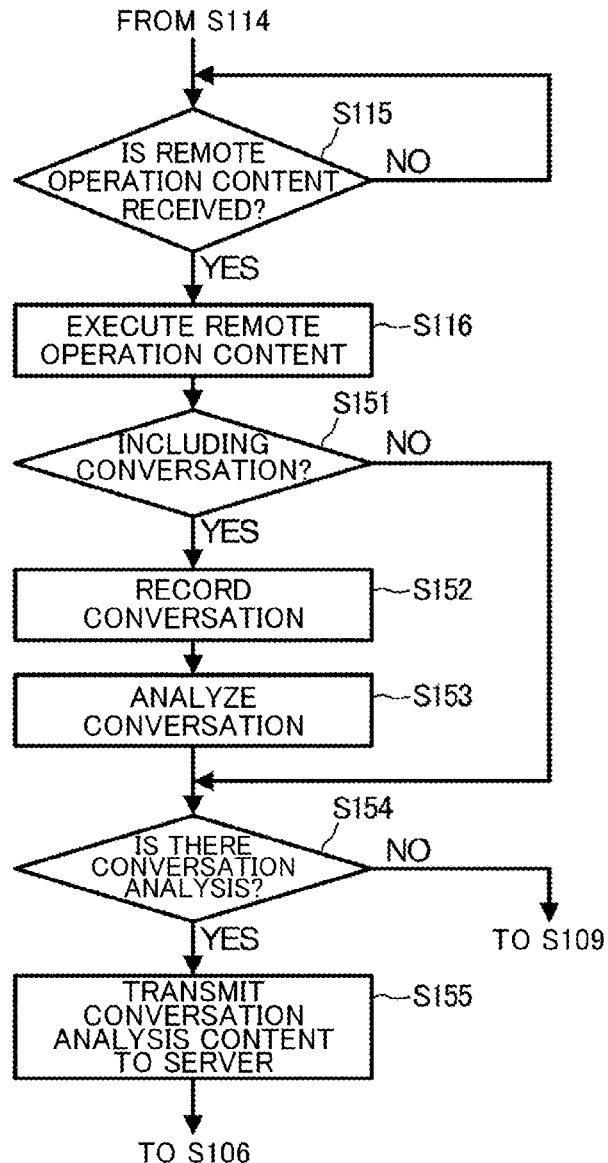
FIG. 29 is a flowchart illustrating an example of an operation of the remote-controlled robot according to the fifth embodiment.

FIG. 29 is a flowchart illustrating an example of an operation of the remote-controlled robot 1 according to the fifth embodiment. In the same drawing, parts similar to those of the first embodiment are omitted.

In a case where it is determined that the remote operation content is received from the robot control terminal 3 in step S115 described above (YES in step S115), the processor 101 of the remote-controlled robot 1 executes the remote operation content in step S116 described above. Here, the processor 101 functions as the interview analysis function unit 143 to determine whether the remote operation content includes an interview, that is, conversation (step S151). In a case where it is determined that the conversation is not included (NO in step S151), the processor 101 shifts to processing of step S154 to be described later.

On the other hand, in a case where it is determined that the conversation is included (YES in step S151), the processor 101 records the conversation content in the temporary storage unit 1033 (step S152). Then, the processor 101 analyzes the recorded conversation contents and stores the analysis result in the temporary storage unit 1033 (step S153).

Thereafter, the processor 101 determines whether the conversation analysis result is stored in the temporary storage unit 1033 (step S154). In a case where it is determined that the conversation analysis result is not stored (NO in step S154), the processor 101 shifts to the processing of the step S109 and transmits measurement information such as blood pressure to the robot control server 2.

On the other hand, when it is determined that the conversation analysis result is stored (YES in step S154), the processor 101 transmits the stored conversation analysis result to the robot control server 2 via the access point 4 by the communication interface 104 (step S155). Here, the processor 101 is assumed to include information for specifying a patient such as a patient name in the conversation analysis result to be transmitted. Next, the processor 101 shifts to the processing in step S106 described above.

Figure 30:
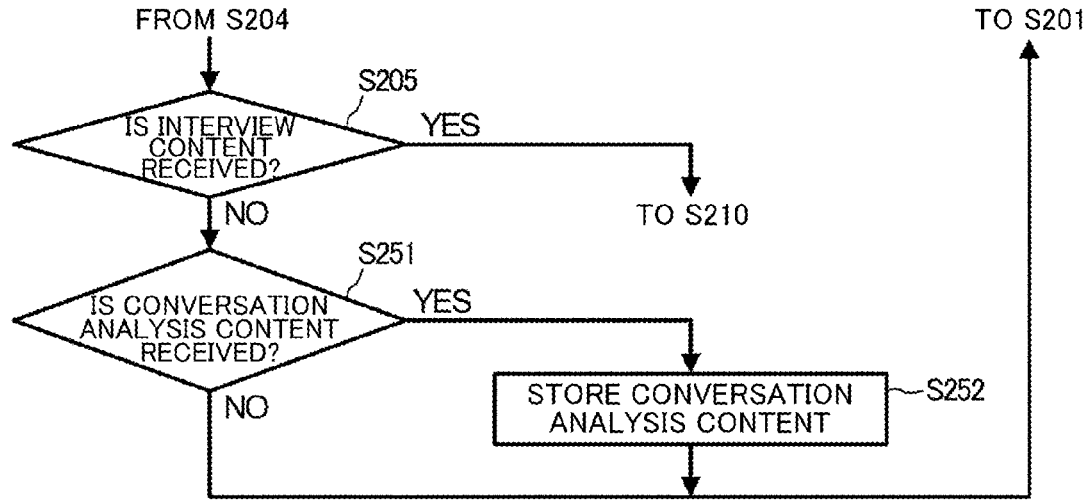
FIG. 30 is a flowchart illustrating an example of an operation of a robot control server in the fifth embodiment.

FIG. 30 is a flowchart illustrating an example of an operation of the robot control server 2 in the fifth embodiment. In the same drawing, parts similar to those of the first embodiment are omitted.

In a case where it is determined that the interview content is not received from the robot control terminal 3 in the step S205 (NO in step S205), the processor 201 of the robot control server 2 further determines whether the conversation analysis content is received from the remote-controlled robot 1 by the communication interface 204 (step S251). In a case where it is determined that the conversation analysis content is not received (NO in step S251), the processor 201 shifts to the processing of step S201 described above.

On the other hand, in a case where it is determined that the conversation analysis content has been received (YES in step S251), the received conversation analysis content is stored in the interview content storage unit 26 of the interview storage unit 2034 (step S252). At this time, the processor 201 specifies the measurement recording table 25 for the patient according to the patient name or the like included in the conversation analysis content, and describes "YES" in the item of the interview. Next, the processor 201 shifts to the processing in step S201 described above.

As described above, in the fifth embodiment, a plurality of tasks to be executed at each task execution place such as a sickroom include a task such as an interview requiring conversation between a task execution target person such as a hospitalized patient and an operator such as a nurse, and the remote-controlled robot 1 further includes the video/ audio communication function unit 142 and the interview analysis function unit 143 that can be provided by the processor 101. The video/audio communication function unit 142 operates as a videophone unit, and when executing a task requiring conversation, the video/audio communication function unit 142 performs video/audio communication with the robot control terminal 3 using the camera 171, the monitor 172, the microphone 173, and the speaker 174. The interview analysis function unit 143 operates as a conversation recording unit, and records a conversation exchanged between the task execution target person and the operator by video/audio communication. In addition, the interview analysis function unit 143 operates as an analysis unit to analyze the contents of the recorded conversation. Further, the interview analysis function unit 143 operates as a saving unit, and saves the analysis result in the interview content storage unit 26 of the robot control server 2.

Therefore, according to the fifth embodiment, the same action and effect as those of the first embodiment can be obtained, and the contents of the interview can be automatically generated and stored from the conversation between the task execution target person and the operator, so that the operator can save the labor of inputting the contents of the interview.

Sixth Embodiment

Next, a sixth embodiment of the present invention will be described. In the present embodiment, when the automatic task of the remote-controlled robot 1 is started, the nurse side is notified of the task execution state, and the nurse side can monitor the task of the remote-controlled robot 1 during the autonomous operation. The same configurations as those of the first embodiment are denoted by the same reference numerals as those of the first embodiment and description thereof will be appropriately omitted.

Figure 31:
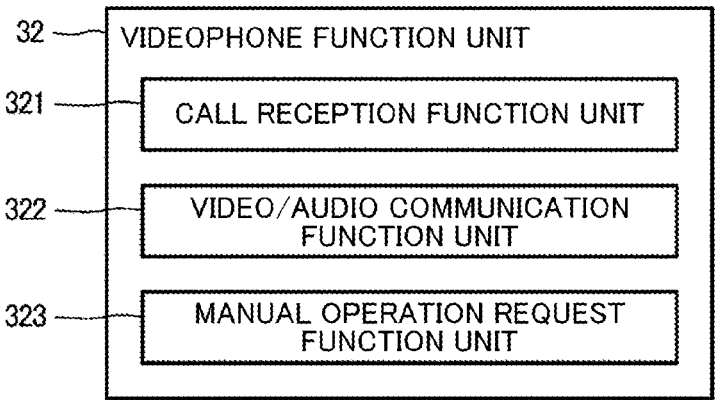
FIG. 31 is a block diagram illustrating an example of a functional configuration of a videophone function unit of a robot control terminal in a sixth embodiment of the present invention.

FIG. 31 is a block diagram illustrating an example of a functional configuration of the videophone function unit 32 of the robot control terminal 3 in the sixth embodiment. In addition to the configuration of the first embodiment, the videophone function unit 32 of the present embodiment includes a manual operation request function unit 323. The manual operation request function unit 323 has a function of monitoring a situation during autonomous operation of the remote-controlled robot 1 by a nurse side. That is, the video acquired by the camera 171 of the remote-controlled robot 1 is displayed on the monitor 342, and the voice acquired by the microphone 173 of the remote-controlled robot 1 is reproduced by the speaker 345.

Figure 32:
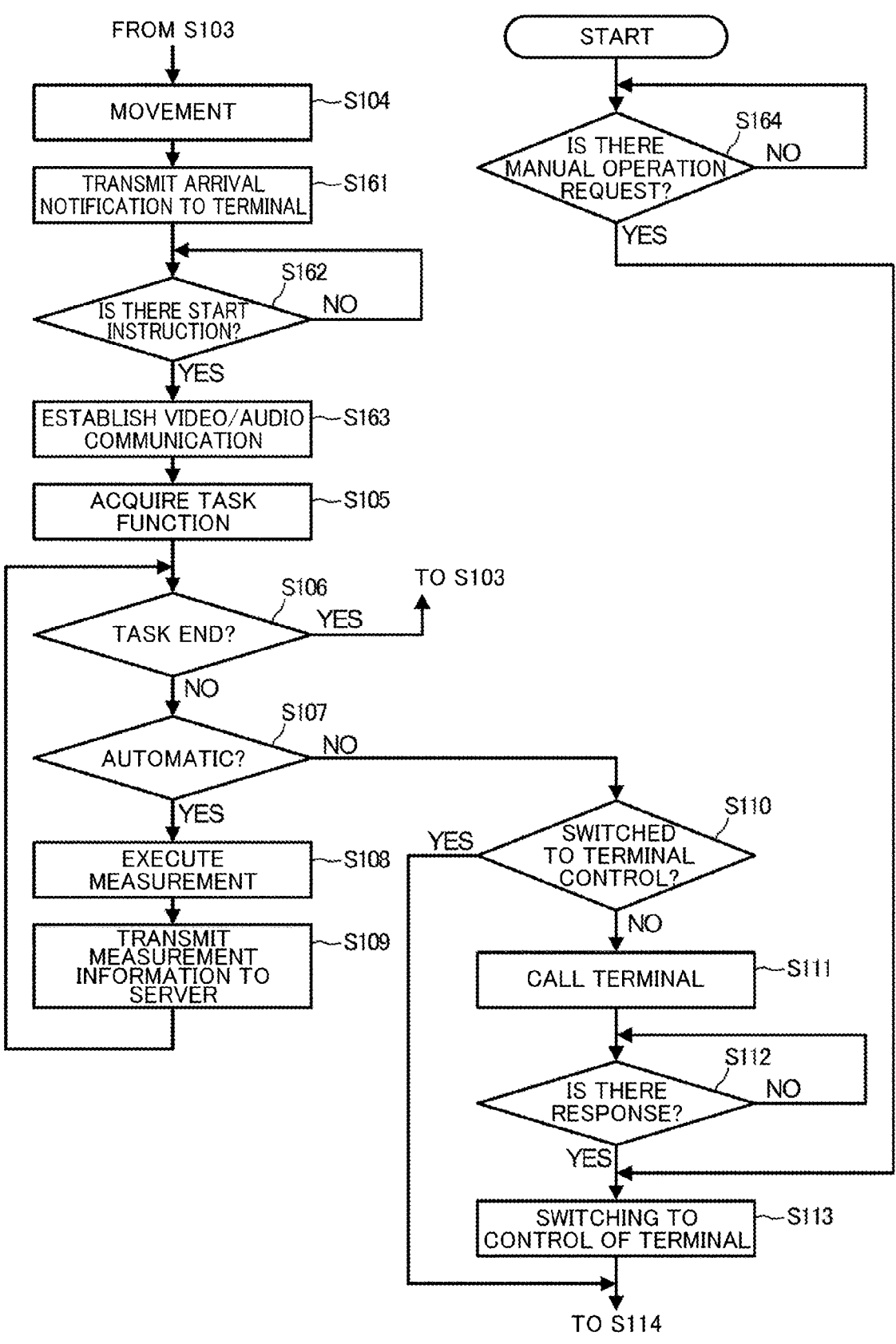
FIG. 32 is a flowchart illustrating an example of an operation of a remote-controlled robot according to the sixth embodiment.

FIG. 32 is a flowchart illustrating an example of an operation of the remote-controlled robot 1 according to the sixth embodiment. In the same drawing, parts similar to those of the first embodiment are omitted.

When the robot moves to the patient in step S104 described above, the processor 101 of the remote-controlled robot 1 functions as the call function unit 141, and transmits an arrival notification to the robot control terminal 3 via the access point 4 by the communication interface 104 (step S161). Then, the processor 101 determines whether a start instruction is received from the robot control terminal 3 by the communication interface 104 (step S162). In a case where it is determined that the start instruction is not received (NO in step S162), the processor 101 continues the processing of the step S162. Thus, the processor 101 waits for the start instruction to be transmitted from the robot control terminal 3.

Figure 33:
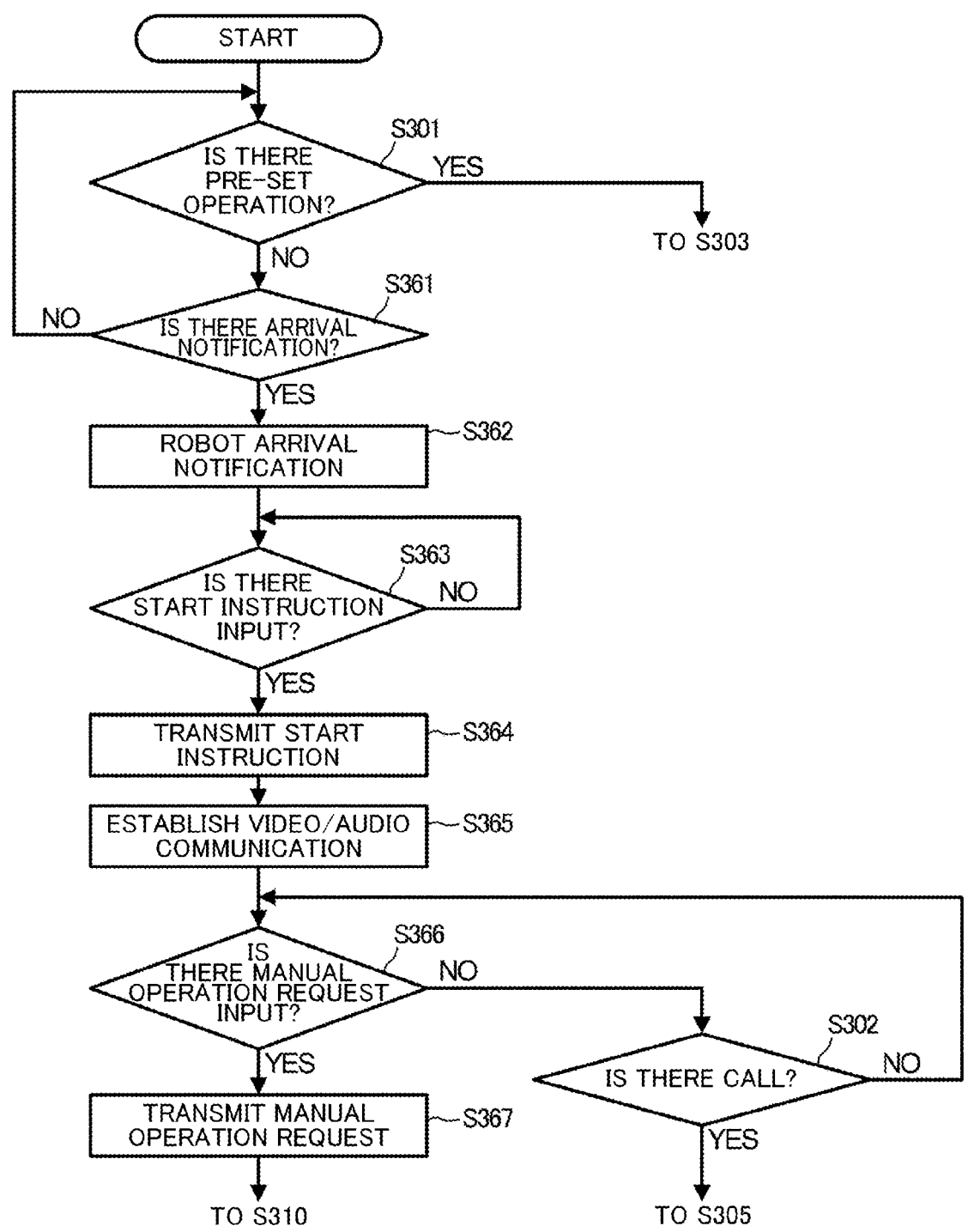
FIG. 33 is a flowchart illustrating an example of an operation of a robot control terminal in the sixth embodiment.

FIG. 33 is a flowchart illustrating an example of an operation of the robot control terminal 3 in the sixth embodiment. In the same drawing, parts similar to those of the first embodiment are omitted.

In a case where the processor 301 of the robot control terminal 3 determines that there is no pre-set operation in step S301 described above (NO in step S301), the processor 301 functions as the call reception function unit 321 in the present embodiment, and determines whether there is an arrival notification from the remote-controlled robot 1 via the communication interface 304 (step S361). In a case where it is determined that there is no arrival notification (NO in step S361), the processor 301 shifts to the processing of step S301 described above. Thus, the processor 301 waits for a pre-set operation or an arrival notification.

In a case where it is determined that there is the arrival notification in step S361 described above (YES in step S361), the processor 301 notifies the nurse that the remote-controlled robot 1 arrives at the patient by the monitor 342 and/or the speaker 345 connected to the input/output interface 305 (step S362). Thereafter, the processor 301 functions as the manual operation request function unit 323, and determines whether there is a start instruction input from a nurse by the keyboard/mouse 341 connected to the input/output interface 305 (step S363). In a case where it is determined that there is no start instruction input (NO in step S363), the processor 301 continues the processing of the step S363. Thus, the processor 301 waits for a start instruction input from the nurse.

In a case where it is determined that there is a start instruction input (YES in step S363), the processor 301 transmits a start instruction to the remote-controlled robot 1 by the communication interface 304 (step S364).

Returning to FIG. 32, in a case where it is determined that the start instruction is received in step S162 described above (YES in step S162), the processor 101 of the remote-controlled robot 1 functions as the video/audio communication function unit 142, and establishes video/audio communication with the robot control terminal 3 via the access point 4 by the communication interface 104 (step S163).

As illustrated in FIG. 33, the processor 301 of the robot control terminal 3 also functions as the video/audio communication function unit 322 after the transmission of the start instruction in step S364 described above, video/audio communication is established by the communication interface 304 (step S365) in concert with the processing of establishing video and audio communication of the remote-controlled robot 1.

Thereafter, the processor 301 determines whether a manual operation request is input from a nurse by the keyboard/mouse 341 connected to the input/output interface 305 (step S366). In a case where it is determined that there is no input of the manual operation request (NO in step S366), the processor 301 determines whether there is a call from the remote-controlled robot 1 after shifting to the processing of step S302 described above. When the processor 301 determines that there is no call from the remote-controlled robot 1 in step S302 described above, the processor 301 shifts to the processing of the step S366. Thus, the processor 301 waits for the input of the manual operation request from the nurse or the call from the remote-controlled robot 1.

Returning to FIG. 32, the processor 101 of the remote-controlled robot 1 shifts to the processing of step S105 described above when the video/audio communication with the robot control terminal 3 is established in step S163 described above, and acquires task function setting contents set for the corresponding patient from the robot control server 2. After that, when it is determined that the task for the patient is not ended in step S106 described above and further it is determined that [Automatic] is set as an automatic/manual flag in step S107 described above, the processor 101 automatically executes the measurement in step S108 described above. Then, the processor 101 transmits the measurement information to the robot control server 2 in step S109 described above, and shifts to the processing of step S106 described above. In this way, the remote-controlled robot 1 executes a task by autonomous operation.

In addition, the processor 101 waits for reception of a manual operation request from the robot control terminal 3 via the access point 4 by the communication interface 104 in parallel with the series of processes described above. That is, the processor 101 determines whether a manual operation request is made from the robot control terminal 3 (step S164). In a case where it is determined that there is no manual operation request (NO in step S164), the processor 101 continues the processing of the step S164.

The state of the autonomous operation of the remote-controlled robot 1 is monitored by the robot control terminal 3 by the established video/audio communication. When it is determined that the nurse needs to switch to the manual operation, for example, in a case where some abnormality occurs, the nurse inputs a manual operation request by the keyboard/mouse 341 of the robot control terminal 3.

In this regard, the processor 301 of the robot control terminal 3 determines that a manual operation request is input from the nurse in step S366 described above (YES in step S366) as illustrated in FIG. 33. In this case, the processor 301 transmits a manual operation request to the remote-controlled robot 1 by the communication interface 304 (step S367). Next, the processor 301 shifts to the processing in step S310 described above.

Returning to FIG. 32, in a case where it is determined that there is a manual operation request from the robot control terminal 3 in step S164 described above (YES in step S164), the processor 101 of the remote-controlled robot 1 shifts to the processing of step S113 described above and switches to the control by the robot control terminal 3.

As described above, in the sixth embodiment, the remote-controlled robot 1 further includes the video/audio communication function unit 142 which can be provided by the processor 101. The video/audio communication function unit 142 operates as a videophone unit, and performs video/audio communication with the robot control terminal 3 when starting a task to be executed by autonomous operation. Then, the task function switching function unit 113 operating as the first switching unit switches to a manual operation in response to a manual operation request from the robot control terminal 3 during the autonomous operation.

Therefore, according to the sixth embodiment, the same operation and effect as those of the first embodiment can be achieved, and an operator monitors the remote-controlled robot 1 in autonomous operation from the robot control terminal 3, and can switch the remote-controlled robot 1 to manual operation as necessary.

OTHER EMBODIMENTS

Note that the present invention is not limited to the above embodiment.

For example, although the second to sixth embodiments have been described as embodiments, they may be suitably combined.

In addition, the robot control server 2 may be configured as one of the robot control terminals 3, or may be configured in another server device such as a hospital management server (not illustrated) connected to the network 5.

Furthermore, the flow of each processing described above is not limited to the procedure described above with reference with the flowchart, the order of some steps may be changed, some steps may be performed concurrently, and the processing contents of some steps may be modified. For example, although the remote-controlled robot 1 acquires the contents of the task function setting table related to each patient when the robot arrives at the patient, the remote-controlled robot 1 may acquire the contents of the task function setting table related to each patient to be patrolled at the start of the patrol in a lump.

In addition, the methods described in each embodiment can be stored as a processing program (software means) that can be executed by a computer in a recording medium, for example, such as a magnetic disk (a floppy (registered trademark) disk, a hard disk, or the like), an optical disc (a CD-ROM, a DVD, a MO, or the like), a semiconductor memory (a ROM, a RAM, a flash memory, or the like) or transmitted and distributed using a communication medium. Further, the program stored on the medium side includes a configuration program for configuring, in the computer, software means (including not only an execution program but also table and data structures) to be executed by the computer. The computer implementing the present device executes the processing described above by reading a program recorded in a recording medium or building the software means using the setting program in some cases and allowing the software means to control an operation thereof. Note that recording media as referred to in the present specification are not limited to recording media for distribution and include storage media such as a magnetic disk or a semiconductor memory provided in a computer or in a device connected via a network.

In short, the present invention is not limited to the embodiment described above and can be variously modified in an implementation stage without departing from the spirit and scope of the invention. In addition, each embodiment may be appropriately combined to the greatest extent feasible and, in such a case, combined effects are produced. Furthermore, the embodiment described above includes inventions in various stages, and various inventions may be extracted through appropriate combinations of the plurality of disclosed constituent elements.

REFERENCE SIGNS LIST

1 Remote-controlled robot
2 Robot control server
3 Robot control terminal
4 Access point
5 Network
6 Blood pressure monitor
10 Remote-controlled robot function unit
11 Robot control unit
12 Function unit storage unit
13 Data transmission unit
14 Videophone function unit
15 Robot drive control unit
20 Robot control server function unit
21 Patrol prediction management unit
22 Task function/measurement data management unit
23 Patrol schedule table
24 Task function setting table 24 Measurement recording table
26 Interview content storage unit
27 Nurse skill information table
30 Robot control terminal function unit
31 Patrol prediction/task setting unit
32 Videophone function unit
33 Robot operation function unit
101,201,301 Processor
102,202,302 Program memory
103,203,303 Data memory
104,204,304 Communication interface
105 Sensor Interface
106,305 Input/output interface
107 Mechanical unit interface
108 Clock
109,205,306 Bus
111 Overall control function unit
112 Patrol management function unit
113 Task function switching function unit
114 Manual operation notification function unit
115 Sleep determination function unit
116 Room occupant determination function unit
117 Operation nurse confirmation function unit
121,122 Task function unit
131 Transmission/reception function unit
141 Call function unit
142 Video/audio communication function unit
143 Interview analysis function unit
151 Arm portion control function unit
152 Drive unit control function unit
161,162 Sensor
171,343 Camera
172,342 Monitor
173,344 Microphone
174,345 Speaker
181 Simple arm portion
182 Drive unit
1031 Facility map storage unit
1032 Control terminal information storage unit
1033,2035,3031 Temporary storage unit
2031 Patrol schedule storage unit
2032 Task function setting storage unit
2033 Measurement record storage unit
2034 Interview storage unit
321 Call reception function unit
322 Video/audio communication function unit
323 Manual operation request function unit
331 Arm portion operation function unit
332 Movement operation function unit
333 Camera operation function unit
341 Keyboard/mouse
346 Operation device

The invention claimed is:

1. A remote-controlled robot configured to autonomously travel to a plurality of task execution places according to a patrol schedule and execute a plurality of tasks at each task execution place, the remote-controlled robot comprising one or more processors configured to execute instructions that cause the remote-controlled robot to perform operations comprising:

acquiring settings of whether to perform autonomous operation or to perform manual operation by an operator from a remote control terminal for each of a plurality of tasks to be performed at each task execution place;

switching between task execution by the autonomous operation and task execution by the manual operation based on the acquired setting;

detecting whether a task execution target person is sleeping, and selecting a set of operations to perform based on the detecting whether the task execution target person is sleeping, the set of tasks being selected from at least (i) an automated task that is automatically performable on the task execution target person without waking the task execution target person in response to detecting that the task execution target person is sleeping and (ii) switching to a manually executable task in response to detecting that the task execution target person is not sleeping.

2. The remote-controlled robot according to claim 1, wherein the plurality of tasks executed at each task execution place is a task executed for a task execution target person, and wherein the one or more processors are further configured to:

detect whether the task execution target person is absent; and correct the patrol schedule in a case where it is detected that the task execution target person is absent.

3. The remote-controlled robot according to claim 1, wherein the plurality of tasks include tasks in which both the autonomous operation and the manual operation are possible, and wherein the one or more processors are further configured to:

acquire an operation skill level of the operator of the remote-controlled robot; and switch between task execution by the autonomous operation and task execution by the manual operation in accordance with the acquired operation skill level for a task in which both the autonomous operation and the manual operation are possible.

4. The remote-controlled robot according to claim 1, wherein the plurality of tasks to be executed at each task execution place include tasks requiring a conversation between a task execution target person and the operator, and wherein the one or more processors are further configured to:

perform video/audio communication with the control terminal when performing the task requiring a conversation;

record a conversation exchanged between the task execution target person and the operator by the video/audio communication;

analyze contents of the recorded conversation; and save an analysis result.

5. The remote-controlled robot according to claim 1, wherein the one or more processors are further configured to perform video/audio communication with the control terminal when starting a task to be performed by the autonomous operation, and switch the operation to the manual operation in response to a manual operation request from the control terminal during the autonomous operation.

6. A remote-controlled robot control system comprising: a remote-controlled robot configured to autonomously travel to a plurality of task execution places according to a patrol schedule and execute a plurality of tasks at each task execution place;

a control terminal configured to manually operate the remote-controlled robot; and a control server accessible by the remote-controlled robot and the control terminal, wherein the control server includes a memory configured to store:

the patrol schedule, and a setting of whether to perform an autonomous operation or to perform a manual operation by an operation of an operator from the control terminal for each of a plurality of tasks to be executed at the task execution place regarding each of the plurality of task execution places, wherein the control terminal includes one or more processors configured to perform setting of the patrol schedule and setting of each of the plurality of tasks in the control server prior to start of operation of the remote-controlled robot, and wherein the remote-controlled robot includes one or more processors configured to acquire a setting for each of the patrol schedule and the plurality of tasks from the control server, and switch between task execution by the autonomous operation and task execution by the manual operation based on the acquired setting;

detect whether a task execution target person is sleeping, and select a set of operations to perform based on the detecting whether the task execution target person is sleeping, the set of tasks being selected from at least (i) an automated task that is automatically performable on the task execution target person without waking the task execution target person in response to detecting that the task execution target person is sleeping and (ii) switching to a manually executable task in response to detecting that the task execution target person is not sleeping.

7. A control method of a remote-controlled robot including a processor and a memory and configured to autonomously travel to a plurality of task execution places according to a patrol schedule and execute a plurality of tasks at each task execution place, the method comprising:

causing the processor to acquire setting whether to perform an autonomous operation or to perform a manual operation by an operation of an operator from a remote control terminal for each of the plurality of tasks to be executed at each task execution place; and causing the processor to switch between task execution by the autonomous operation and task execution by the manual operation based on the acquired setting;

causing the processor to detect whether a task execution target person is sleeping, and causing the processor to select a set of operations to perform based on the detecting whether the task execution target person is sleeping, the set of tasks being selected from at least (i) an automated task that is automatically performable on the task execution target person without waking the task execution target person in response to detecting that the task execution target person is sleeping and (ii) switching to a manually executable task in response to detecting that the task execution target person is not sleeping.

\* \* \* \* \*